United States Patent
Vogelstein et al.

(10) Patent No.: US 9,476,095 B2
(45) Date of Patent: Oct. 25, 2016

(54) SAFE SEQUENCING SYSTEM

(75) Inventors: Bert Vogelstein, Baltimore, MD (US); Kenneth W. Kinzler, Baltimore, MD (US); Nickolas Papadopoulos, Towson, MD (US); Isaac Kinde, Beaumont, CA (US)

(73) Assignee: The Johns Hopkins University, Baltimore, MD (US)

( * ) Notice: Subject to any disclaimer, the term of this patent is extended or adjusted under 35 U.S.C. 154(b) by 106 days.

(21) Appl. No.: 14/111,715

(22) PCT Filed: Apr. 12, 2012

(86) PCT No.: PCT/US2012/033207
§ 371 (c)(1),
(2), (4) Date: Apr. 29, 2014

(87) PCT Pub. No.: WO2012/142213
PCT Pub. Date: Oct. 18, 2012

(65) Prior Publication Data
US 2014/0227705 A1    Aug. 14, 2014

Related U.S. Application Data

(60) Provisional application No. 61/476,150, filed on Apr. 15, 2011, provisional application No. 61/484,482, filed on May 10, 2011.

(51) Int. Cl.
C12Q 1/68         (2006.01)
C07H 21/02        (2006.01)

(52) U.S. Cl.
CPC ........... *C12Q 1/6876* (2013.01); *C12Q 1/6869* (2013.01); *C12Q 1/6874* (2013.01); *C12Q 2563/179* (2013.01); *C12Q 2600/158* (2013.01)

(58) Field of Classification Search
CPC .......... C12Q 2535/122; C12Q 1/6869; C12Q 2563/179; C12Q 2565/514; C12Q 1/6876
See application file for complete search history.

(56) References Cited

U.S. PATENT DOCUMENTS

| | | | |
|---|---|---|---|
| 6,746,845 B2 | 6/2004 | Kinzler et al. | |
| 8,481,292 B2 | 7/2013 | Casbon et al. | |
| 2003/0148335 A1 | 8/2003 | Shen et al. | |
| 2006/0263789 A1 | 11/2006 | Kincaid | |
| 2007/0020640 A1* | 1/2007 | McCloskey | C12Q 1/686 435/6.16 |
| 2007/0269805 A1 | 11/2007 | Hogers | |
| 2009/0215062 A1* | 8/2009 | Lee | C12Q 1/6806 435/6.11 |
| 2009/0233802 A1* | 9/2009 | Bignell | C12Q 1/6874 506/2 |
| 2010/0273219 A1 | 10/2010 | May et al. | |

FOREIGN PATENT DOCUMENTS

WO    02059355 A2    8/2002
WO    2009152928 A2    12/2009

OTHER PUBLICATIONS

Boyd, S.D. et al., Science Translat. Med., vol. 1, 12ra23, pp. 1-8 (2009).*
Boyd, S.D. et al., Science Translat. Med., vol. 1, 12ra23, Supplementary material, pp. 1-30 (2009).*
International Search Report and Written Opinion mailed Nov. 28, 2012 (PCT/US2012/033207); ISA/KR.
Karow, "Hopkins Team Develops method to Improve Rare Mutation Detection for Early Cancer Dx," Genomeweb, Jun. 1, 2011.
Casbon et al., "A method for counting PCR template molecules with application to next-generation sequencing," Nucleic Acids Research, 2011, 1-8.
Kivioja et al., "Counting absolute numbers of molecules using unique molecular identifiers," Nature Methods, Jan. 2012, vol. 9, No. 1, pp. 72-74.
Extended European Search Report issued in related European Application No. 12772013.4, dated Sep. 17, 2014.
Office Action mailed Jan. 6, 2016 in related U.S. Appl. No. 14/814,030.

* cited by examiner

*Primary Examiner* — Teresa Strzelecka
(74) *Attorney, Agent, or Firm* — Banner & Witcoff, Ltd.

(57) ABSTRACT

The identification of mutations that are present in a small fraction of DNA templates is essential for progress in several areas of biomedical research. Though massively parallel sequencing instruments are in principle well-suited to this task, the error rates in such instruments are generally too high to allow confident identification of rare variants. We here describe an approach that can substantially increase the sensitivity of massively parallel sequencing instruments for this purpose. One example of this approach, called "Safe-SeqS" for (Safe-Sequencing System) includes (i) assignment of a unique identifier (UID) to each template molecule; (ii) amplification of each uniquely tagged template molecule to create UID-families; and (iii) redundant sequencing of the amplification products. PCR fragments with the same UID are truly mutant ("super-mutants") if ≥95% of them contain the identical mutation. We illustrate the utility of this approach for determining the fidelity of a polymerase, the accuracy of oligonucleotides synthesized in vitro, and the prevalence of mutations in the nuclear and mitochondrial genomes of normal cells.

34 Claims, 7 Drawing Sheets

SAFE SEQUENCING SYSTEM

This invention was made using support from the National Institutes of Health, grants CA62924, CA43460, and CA57345. Certain rights to the invention are retained by the U.S. government under the terms of the grant.

TECHNICAL FIELD OF THE INVENTION

This invention is related to the area of nucleic acid sequencing. In particular, it relates to manipulative and analytic steps for analyzing and verifying the products of low frequency events.

BACKGROUND OF THE INVENTION

Genetic mutations underlie many aspects of life and death—through evolution and disease, respectively. Accordingly, their measurement is critical to several fields of research. Luria and Delbrück's classic fluctuation analysis is a prototypic example of the insights into biological processes that can be gained simply by counting the number of mutations in carefully controlled experiments (1). Counting de novo mutations in humans, not present in their parents, have similarly led to new insights into the rate at which our species can evolve (2, 3). Similarly, counting genetic or epigenetic changes in tumors can inform fundamental issues in cancer biology (4). Mutations lie at the core of current problems in managing patients with viral diseases such as AIDS and hepatitis by virtue of the drug-resistance they can cause (5, 6). Detection of such mutations, particularly at a stage prior to their becoming dominant in the population, will likely be essential to optimize therapy. Detection of donor DNA in the blood of organ transplant patients is an important indicator of graft rejection and detection of fetal DNA in maternal plasma can be used for prenatal diagnosis in a non-invasive fashion (7, 8). In neoplastic diseases, which are all driven by somatic mutations, the applications of rare mutant detection are manifold; they can be used to help identify residual disease at surgical margins or in lymph nodes, to follow the course of therapy when assessed in plasma, and perhaps to identify patients with early, surgically curable disease when evaluated in stool, sputum, plasma, and other bodily fluids (9-11).

These examples highlight the importance of identifying rare mutations for both basic and clinical research. Accordingly, innovative ways to assess them have been devised over the years. The first methods involved biologic assays based on prototrophy, resistance to viral infection or drugs, or biochemical assays (1, 12-18). Molecular cloning and sequencing provided a new dimension to the field, as it allowed the type of mutation, rather than simply its presence, to be identified (19-24). Some of the most powerful of these newer methods are based on Digital PCR, in which individual molecules are assessed one-by-one (25). Digital PCR is conceptually identical to the analysis of individual clones of bacteria, cells, or virus, but is performed entirely in vitro with defined, inanimate reagents. Several implementations of Digital PCR have been described, including the analysis of molecules arrayed in multi-well plates, in polonies, in microfluidic devices, and in water-in-oil emulsions (25-30). In each of these technologies, mutant templates are identified through their binding to oligonucleotides specific for the potentially mutant base.

Massively parallel sequencing represents a particularly powerful form of Digital PCR in that hundreds of millions of template molecules can be analyzed one-by-one. It has the advantage over conventional Digital PCR methods in that multiple bases can be queried sequentially and easily in an automated fashion. However, massively parallel sequencing cannot generally be used to detect rare variants because of the high error rate associated with the sequencing process. For example, with the commonly used Illumina sequencing instruments, this error rate varies from ~1% (31, 32) to ~0.05% (33, 34), depending on factors such as the read length (35), use of improved base calling algorithms (36-38) and the type of variants detected (39). Some of these errors presumably result from mutations introduced during template preparation, during the pre-amplification steps required for library preparation and during further solid-phase amplification on the instrument itself. Other errors are due to base mis-incorporation during sequencing and base-calling errors. Advances in base-calling can enhance confidence (e.g., (36-39)), but instrument-based errors are still limiting, particularly in clinical samples wherein the mutation prevalence can be 0.01% or less (11). In the work described below, we show how templates can be prepared and the sequencing data obtained from them can be more reliably interpreted, so that relatively rare mutations can be identified with commercially available instruments.

There is a continuing need in the art to improve the sensitivity and accuracy of sequence determinations for investigative, clinical, forensic, and genealogical purposes.

SUMMARY OF THE INVENTION

According to one aspect of the invention a method analyzes nucleic acid sequences. A unique identifier (UID) nucleic acid sequence is attached to a first end of each of a plurality of analyte nucleic acid fragments to form uniquely identified analyte nucleic acid fragments. Nucleotide sequence of a uniquely identified analyte nucleic acid fragment is redundantly determined, wherein determined nucleotide sequences which share a UID form a family of members. A nucleotide sequence is identified as accurately representing an analyte nucleic acid fragment when at least 1% of members of the family contain the sequence.

According to another aspect of the invention a method analyzes nucleic acid sequences. A unique identifier sequence (UID) is attached to a first end of each of a plurality of analyte DNA fragments using at least two cycles of amplification with first and second primers to form uniquely identified analyte DNA fragments. The UIDs are in excess of the analyte DNA fragments during amplification. The first primers comprise a first segment complementary to a desired amplicon; a second segment containing the UID; and a third segment containing a universal priming site for subsequent amplification. The second primers comprise a universal priming site for subsequent amplification. Each cycle of amplification attaches one universal priming site to a strand. The uniquely identified analyte DNA fragments are amplified to form a family of uniquely identified analyte DNA fragments from each uniquely identified analyte DNA fragment. Nucleotide sequences of a plurality of members of the family are determined.

Another aspect of the invention is a method to analyze DNA using endogenous unique identifier sequences (UIDs). Fragmented analyte DNA is obtained comprising fragments of 30 to 2000 bases, inclusive. Each end of a fragment forms an endogenous UID for the fragment. Adapter oligonucleotides are attached to ends of the fragments to form adapted fragments. Fragments representing one or more selected genes are optionally enriched by means of capturing a subset of the fragments using capture oligonucleotides complementary to selected genes in the analyte DNA or by amplifying fragments complementary to selected genes. The adapted fragments are amplified using primers complementary to the adapter oligonucleotides to form families of adapted fragments. Nucleotide sequence is determined of a plurality of members of a family. Nucleotide sequences of the plurality of members of the family are compared. A nucleotide sequence is identified as accurately representing an analyte DNA fragment when at least a 1% of members of the family contain the sequence.

Still another aspect of the invention is a composition comprising population of primer pairs, wherein each pair comprises a first and second primer for amplifying and identifying a gene or gene portion. The first primer comprises a first portion of 10-100 nucleotides complementary to the gene or gene portion and a second portion of 10 to 100 nucleotides comprising a site for hybridization to a third primer. The second primer comprises a first portion of 10-100 nucleotides complementary to the gene or gene portion and a second portion of 10 to 100 nucleotides comprising a site for hybridization to a fourth primer. Interposed between the first portion and the second portion of the second primer is a third portion consisting of 2 to 4000 nucleotides forming a unique identifier (UID). The unique identifiers in the population have at least 4 different sequences. The first and second primers are complementary to opposite strands of the gene or gene portion. A kit may comprise the population of primers and the third and fourth primers complementary to the second portions of each of the first and second primers.

These and other embodiments which will be apparent to those of skill in the art upon reading the specification provide the art with tools and methods for sensitively and accurately determining nucleic acid features or sequences.

DETAILED DESCRIPTION OF THE INVENTION

Figure 1:
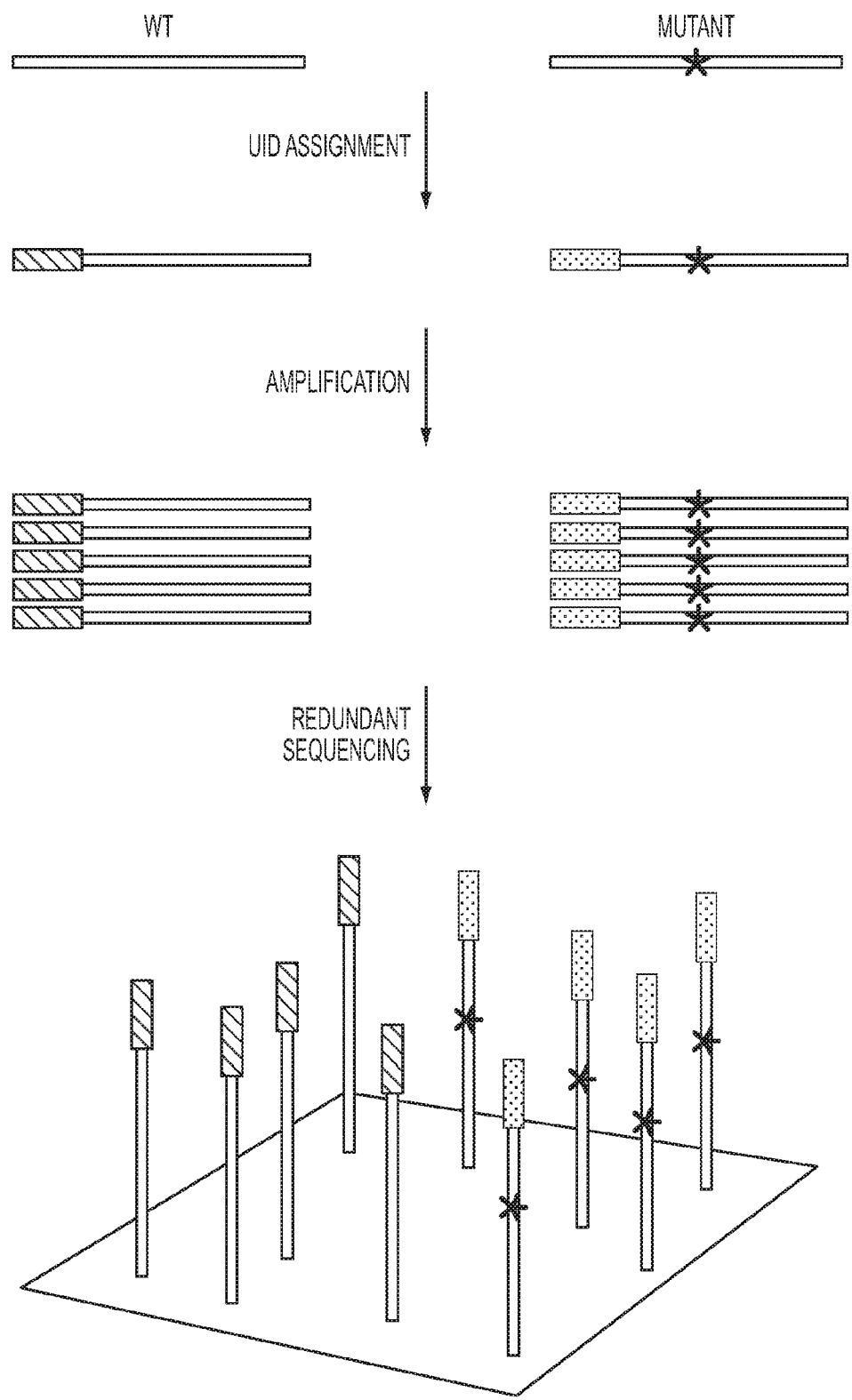
FIG. 1. Essential Elements of Safe-SeqS. In the first step, each fragment to be analyzed is assigned a unique identification (UID) sequence (metal hatch or stippled bars). In the second step, the uniquely tagged fragments are amplified, producing UID-families, each member of which has the same UID. A super-mutant is defined as a UID-family in which ≥95% of family members have the same mutation.

The inventors have developed an approach, called "Safe-SeqS" (from Safe-Sequencing System). In one embodiment it involves two basic steps (FIG. 1). The first is the assignment of a Unique Identifier (UID) to each nucleic acid template molecule to be analyzed. The second is the amplification of each uniquely tagged template, so that many daughter molecules with the identical sequence are generated (defined as a UID-family). If a mutation pre-existed in the template molecule used for amplification, that mutation should be present in a certain proportion, or even all, of daughter molecules containing that UID (barring any subsequent replication or sequencing errors). A UID-family in which every family member (or a certain predetermined proportion) has an identical mutation is called a "supermutant." Mutations not occurring in the original templates, such as those occurring during the amplification steps or through errors in base-calling, should not give rise to supermutants, i.e., will not be present at the pre-determined frequency in a UID family. In other embodiments, amplification is not necessary.

The approach can be employed for any purpose where a very high level of accuracy and sensitivity is required from sequence data. As shown below, the approach can be used to assess the fidelity of a polymerase, the accuracy of in vitro synthesized nucleic acid synthesis, and the prevalence of mutations in nuclear or mitochondrial nucleic acids of normal cells. The approach may be used to detect and/or quantify mosaics and somatic mutations.

Fragments of nucleic acids may be obtained using a random fragment forming technique such as mechanical shearing, sonicating, or subjecting nucleic acids to other physical or chemical stresses. Fragments may not be strictly random, as some sites may be more susceptible to stresses than others. Endonucleases that randomly or specifically fragment may also be used to generate fragments. Size of fragments may vary, but desirably will be in ranges between 30 and 5,000 basepairs, between 100 and 2,000, between 150 and 1,000, or within ranges with different combinations of these endpoints. Nucleic acids may be, for example, RNA or DNA. Modified forms of RNA or DNA may also be used.

Attachment of an exogenous UID to an analyte nucleic acids fragment may be performed by any means known in the art, including enzymatic, chemical, or biologic. One means employs a polymerase chain reaction. Another means employs a ligase enzyme. The enzyme may be mammalian or bacterial, tier example. Ends of fragments may be repaired prior to joining using other enzymes such as Klenow Fragment of T4 DNA Polymerase. Other enzymes which may be used for attaching are other polymerase enzymes. An UID may be added to one or both ends of the fragments. A UID may be contained within a nucleic acid molecule that contains other regions for other intended functionality. For example, a universal priming site may be added to permit later amplification. Another additional site may be a region of complementarity to a particular region or gene in the analyte nucleic acids. A UID may be from 2 to 4,000, from 100 to 1000, from 4 to 400, bases in length, for example.

UIDs may be made using random addition of nucleotides to form a short sequence to be used as an identifier. At each position of addition, a selection from one of four deoxyribonucleotides may be used. Alternatively a selection from one of three, two, or one deoxyribonucleotides may be used. Thus the UID may be fully random, somewhat random, or non-random in certain positions. Another manner of making UIDs utilizes pre-determined nucleotides assembled on a chip. In this manner of making, complexity is attained in a planned manner. It may be advantageous to attach a UID to each end of a fragment, increasing the complexity of the UID population on fragments.

A cycle of polymerase chain reaction for adding exogenous UID refers to the thermal denaturation of a double stranded molecule, the hybridization of a first primer to a resulting single strand, the extension of the primer to form a new second strand hybridized to the original single strand. A second cycle refers to the denaturation of the new second strand from the original single strand, the hybridization of a second primer to the new second strand, and the extension of the second primer to form a new third strand, hybridized to the new second strand. Multiple cycles may be required to increase efficiency, for example, when analyte is dilute or inhibitors are present.

In the case of endogenous UIDs, adapters can be added to the ends of fragments by ligation. Complexity of the analyte fragments can be decreased by a capture step, either on a solid phase or in liquid step. Typically the capture step will employ hybridization to probes representing a gene or set of genes of interest. If on a solid phase, non-binding fragments are separated from binding fragments. Suitable solid phases known in the art include filters, membranes, beads, columns, etc. If in a liquid phase, a capture reagent can be added which binds to the probes, for example through a biotin-avidin type interaction. After capture, desired fragments can be eluted for further processing. The order of adding adapters and capturing is not critical. Another means of reducing the complexity of the analyte fragments involves amplification of one or more specific genes or regions. One way to accomplish this is to use inverse PCR. Primers can be used which are gene-specific, thus enriching while forming libraries. Optionally, the gene-specific primers can contain grafting sequences for subsequent attachment to a massively parallel sequencing platform.

Because endogenous UIDs provide a limited number of unique possibilities, depending on the fragment size and sequencing read length, combinations of both endogenous and exogenous UIDs can be used. Introducing additional sequences when amplifying would increase the available UIDs and thereby increase sensitivity. For example, before amplification, the template can be split into 96 wells, and 96 different primers could be used during the amplification. This would effectively increase the available UIDs 96-fold, because up to 96 templates with the same endogenous UID could be distinguished. This technique can also be used with exogenous UIDs, so that each well's primers adds a unique, well-specific sequence to the amplification products. This can improve the specificity of detection of rare templates.

Amplification of fragments containing a UID can be performed according to known techniques to generate families of fragments. Polymerase chain reaction can be used. Other amplification methods can also be used, as is convenient. Inverse PCR may be used, as can rolling circle amplification. Amplification of fragments typically is done using primers that are complementary to priming sites that are attached to the fragments at the same time as the UIDs. The priming sites are distal to the UIDs, so that amplification includes the UIDs. Amplification forms a family of fragments, each member of the family sharing the same UID. Because the diversity of UIDs is greatly in excess of the diversity of the fragments, each family should derive from a single fragment molecule in the analyte. Primers used for the amplification may be chemically modified to render them more resistant to exonucleases. One such modification is the use of phosphorothioate linkages between one or more 3' nucleotides. Another employs boranophosphates.

Family members are sequenced and compared to identify any divergencies within a family. Sequencing is preferably performed on a massively parallel sequencing platform, many of which are commercially available. If the sequencing platform requires a sequence for "grafting," i.e., attachment to the sequencing device, such a sequence can be added during addition of UIDs or adapters or separately. A grafting sequence may be part of a UID primer, a universal primer, a gene target-specific primer, the amplification primers used for making a family, or separate. Redundant sequencing refers to the sequencing of a plurality of members of a single family.

A threshold can be set for identifying a mutation in an analyte. If the "mutation" appears in all members of a family, then it derives from the analyte. If it appears in less than all members, then it may have been introduced during the analysis. Thresholds for calling a mutation may be set, for example, at 1%, 5%, 10%, 20%, 30%, 40%, 50%, 60%, 70%, 80%, 90%, 95%, 97%, 98%, or 100%. Thresholds will be set based on the number of members of a family that are sequenced and the particular purpose and situation.

Populations of primer pairs are used to attach exogenous UIDs. The first primer comprises a first portion of 10-100 nucleotides complementary to the gene or gene portion and a second portion of 10 to 100 nucleotides comprising a site for hybridization to a third primer. The second primer comprises a first portion of 10-100 nucleotides complementary to the gene or gene portion and a second portion of 10 to 100 nucleotides comprising a site for hybridization to a fourth primer. Interposed between the first portion and the second portion of the second primer is a third portion consisting of 2 to 4,000 nucleotides forming a unique identifier (UID). The unique identifiers in the population have at least 4, at least 16, at least 64, at least 256, at least 1,024, at least 4,096, at least 16,384, at least 65,536, at least 262,144, at least 1,048,576, at least 4,194,304 at least 16,777,216, or at least 67,108,864 different sequences. The first and second primers are complementary to opposite strands of the gene or gene portion. A kit can be made containing both the primers for attaching exogenous UIDs as well as amplification primers, i.e., the third and fourth primers complementary to the second portions of each of the first and second primers. The third and fourth primers can optionally contain additional grafting or indexing sequences. The UID may comprise randomly selected sequences, pre-defined nucleotide sequences, or both randomly selected sequences and pre-defined nucleotides. If both, these can be joined together in blocks or interspersed.

The methods of analysis can be used to quantitate as well as to determine a sequence. For example, the relative abundance of two analyte DNA fragments may be compared.

The results described below in the examples demonstrate that the Safe-SeqS approach can substantially improve the accuracy of massively parallel sequencing (Tables 1 and 2). It can be implemented through either endogenous or exogenously introduced UIDs and can be applied to virtually any sample preparation workflow or sequencing platform. As demonstrated here, the approach can easily be used to identify rare mutants in a population of DNA templates, to measure polymerase error rates, and to judge the reliability of oligonucleotide syntheses. One of the advantages of the strategy is that it yields the number of templates analyzed as well as the fraction of templates containing variant bases. Previously described in vitro methods for the detection of small numbers of template molecules (e.g., (29, 50)) allow the fraction of mutant templates to be determined but cannot determine the number of mutant and normal templates in the original sample.

It is of interest to compare Safe-SeqS to other approaches for reducing errors in next generation sequencing. As mentioned above, in the background of the invention, sophisticated algorithms to increase the accuracy of base-calling have been developed (e.g., (36-39)). These can certainly reduce false positive calls, but their sensitivity is still limited by artifactual mutations occurring during the PCR steps required for library preparation as well as by (a reduced number of) base-calling errors. For example, the algorithm employed in the current study used very stringent criteria for base-calling and was applied to short read-lengths, but was still unable to reduce the error rate to less than an average of $2.0 \times 10^{-4}$ errors/bp. This error frequency is at least as low as those reported with other algorithms. To improve sensitivity further, these base-calling improvements can be used together with Safe-SeqS. Travers et al. have described another powerful strategy for reducing errors (51). With this technology, both strands of each template molecule are sequenced redundantly after a number of preparative enzymatic steps. However, this approach can only be performed on a specific instrument. Moreover, for many clinical applications, there are relatively few template molecules in the initial sample and evaluation of nearly all of them is required to obtain the requisite sensitivity. The approach described here with exogenously introduced UIDs (FIG. 3) fulfills this requirement by coupling the UID assignment step with a subsequent amplification in which few molecules are lost. Our endogenous UID approaches (FIG. 2 and FIG. 5) and the one described by Travers et al. are not ideally suited for this purpose because of the inevitable losses of template molecules during the ligation and other preparative steps.

How do we know that the mutations identified by conventional analyses in the current study represent artifacts rather than true mutations in the original templates? Strong evidence supporting this is provided by the observation that the mutation prevalence in all but one experiment was similar—$2.0 \times 10^{-4}$ to $2.4 \times 10^{-4}$ mutations/bp (Tables 1 and 2). The exception was the experiment with oligonucleotides synthesized from phosphoramidites, in which the error of the synthetic process was apparently higher than the error rate of conventional Illumina analysis when used with stringent base-calling criteria. In contrast, the mutation prevalence of Safe-SeqS varied much more, from 0.0 to $1.4 \times 10^{-5}$ mutations/bp, depending on the template and experiment. Moreover, the mutation prevalence measured by Safe-SeqS in the most controlled experiment, in which polymerase fidelity was measured (Table 2A), was almost identical to that predicted from previous experiments in which polymerase fidelity was measured by biological assays. Our measurements of mutation prevalence in the DNA from normal cells are consistent with some previous experimental data. However, estimates of these prevalences vary widely and may depend on cell type and sequence analyzed (see SI text). We therefore cannot be certain that the few mutations revealed by Safe-SeqS represented errors occurring during the sequencing process rather than true mutations present in the original DNA templates. Potential sources of error in the Safe-SeqS process are described in the SI text.

Another potential application of Safe-SeqS is the minimization of PCR contamination, a serious problem for clinical laboratories. With endogenous or exogenous UID assignment, the UIDs of mutant templates can simply be compared to those identified in prior experiments; the probability that the same mutation from two independent samples would have the same UID in different experiments is negligible when mutations are infrequent. Additionally, with exogenous UIDs, a control experiment with the same template but without the UID assigning PCR cycles (FIG. 3) can ensure that no DNA contamination is present in that template preparation; no template should be amplified in the absence of UID assignment cycles and thus no PCR product of the proper size should be observed.

Like all techniques, Safe-SeqS has limitations. For example, we have demonstrated that the exogenous UIDs strategy can be used to analyze a single amplicon in depth. This technology may not be applicable to situations wherein multiple amplicons must be analyzed from a sample containing a limited number of templates. Multiplexing in the UID assignment cycles (FIG. 3) may provide a solution to this challenge. A second limitation is that the efficiency of amplification in the UID assignment cycles is critical for the success of the method. Clinical samples may contain inhibitors that reduce the efficiency of this step. This problem can presumably be overcome by performing more than two cycles in UID assignment PCR step (FIG. 3), though this would complicate the determination of the number of templates analyzed. The specificity of Safe-SeqS is currently limited by the fidelity of the polymerase used in the UID assignment PCR step, i.e., $8.8 \times 10^{-7}$ mutations/bp in its current implementation with two cycles. Increasing the number of cycles in the UID assignment PCR step to five would decrease the overall specificity to $\sim 2 \times 10^{-6}$ mutations/bp. However, this specificity can be increased by requiring more than one super-mutant for mutation identification—the probability of introducing the same artifactual mutation twice or three times would be exceedingly low ($[2 \times 10^{-6}]^2$ or $[2 \times 10^{-6}]^3$, respectively). In sum, there are several simple ways to perform Safe-SeqS variations and analysis variations to realize the needs of specific experiments.

Luria and Delbrück, in their classic paper in 1943, wrote that their "prediction cannot be verified directly, because what we observe, when we count the number of resistant bacteria in a culture, is not the number of mutations which have occurred but the number of resistant bacteria which have arisen by multiplication of those which mutated, the amount of multiplication depending on how far back the mutation occurred." The Safe-SeqS procedure described here can verify such predictions because the number as well as the time of occurrence of each mutation can be estimated from the data, as noted in the experiments on polymerase fidelity. In addition to templates generated by polymerases in vitro, the same approach can be applied to DNA from bacteria, viruses, and mammalian cells. We therefore expect that this strategy will provide definitive answers to a variety of important biomedical questions.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Endogenous UIDs

Figure 2:
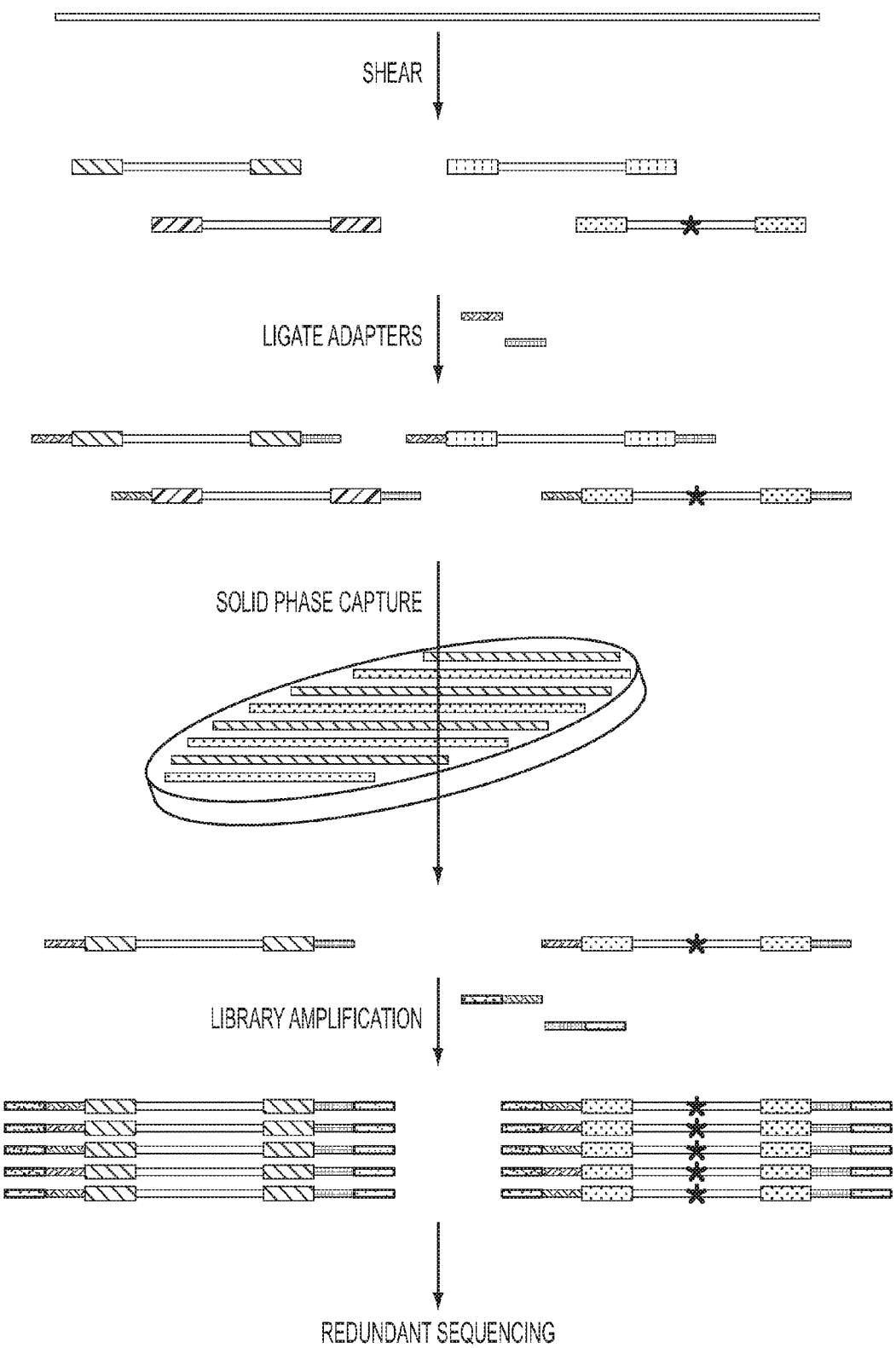
FIG. 2. Safe-SeqS with Endogenous UIDs Plus Capture. The sequences of the ends of each fragment produced by random shearing (variously shaded bars) serve as the unique identifiers (UIDs). These fragments are ligated to adapters (earth hatched and cross hatched bars) so they can subsequently be amplified by PCR. One uniquely identifiable fragment is produced from each strand of the double-stranded template; only one strand is shown. Fragments of interest are captured on a solid phase containing oligonucleotides complementary to the sequences of interest. Following PCR amplification to produce UID-families with primers containing 5' "grafting" sequences (adhesive filled and light stippled bars), sequencing is performed and super-mutants are defined as in FIG. 1.
Figure 5:
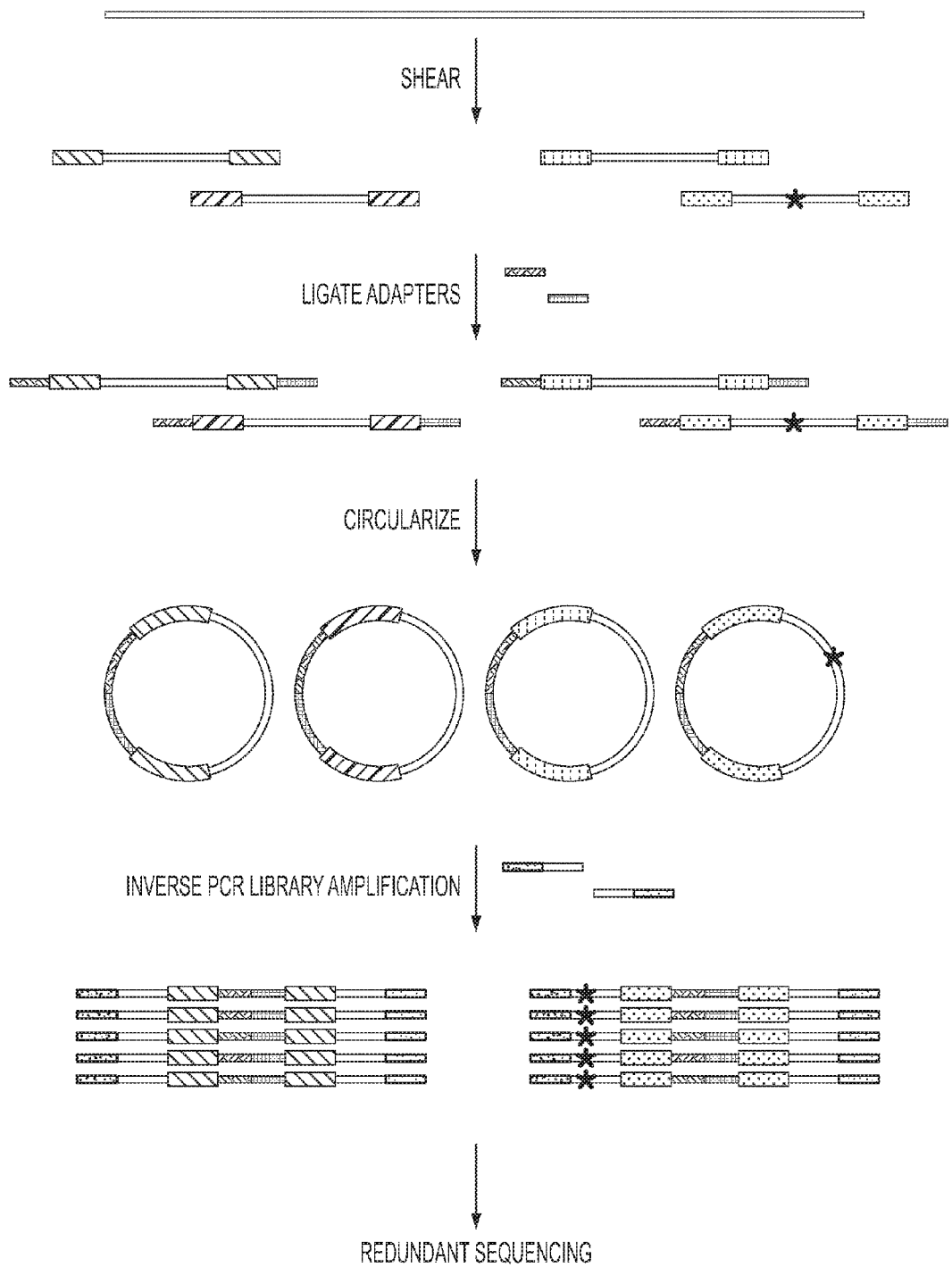
FIG. 5. Safe-SeqS with endogenous UIDs plus inverse PCR. The sequence of the ends of each fragment produced by random shearing serve as unique identifiers (UIDs; variously shaded bars). These fragments are ligated to adapters (earth hatched and cross hatched bars) as in a standard Illumina library preparation. One uniquely tagged fragment is produced from each strand of the double-stranded template; only one strand is shown. Following circularization with a ligase, inverse PCR is performed with gene-specific primers that also contain 5' "grafting" sequences (adhesive filled and lightly stippled bars). This PCR produces UID-families which are directly sequenced. Super-mutants are defined as in FIG. 1.

UIDs, sometimes called barcodes or indexes, can be assigned to nucleic acid fragments in many ways. These include the introduction of exogenous sequences through PCR (40, 41) or ligation (42, 43). Even more simply, randomly sheared genomic DNA inherently contains UIDs consisting of the sequences of the two ends of each sheared fragment (FIG. 2 and FIG. 5). Paired-end sequencing of these fragments yields UID-families that can be analyzed as described above. To employ such endogenous UIDs in Safe-SeqS, we used two separate approaches: one designed to evaluate many genes simultaneously and the other designed to evaluate a single gene fragment in depth (FIG. 2 and FIG. 5, respectively).

For the evaluation of multiple genes, we ligated standard Illumina sequencing adapters to the ends of sheared DNA fragments to produce a standard sequencing library, then captured genes of interest on a solid phase (44). In this experiment, a library made from the DNA of ~15,000 normal cells was used, and 2,594 bp from six genes were targeted for capture. After excluding known single nucleotide polymorphisms, 25,563 apparent mutations, corresponding to $2.4 \times 10^{-4} \pm$mutations/bp, were also identified (Table 1). Based on previous analyses of mutation rates in human cells, at least 90% of these apparent mutations were likely to represent mutations introduced during template and library preparation or base-calling errors. Note that the error rate determined here ($2.4 \times 10^{-4}$ mutations/bp) is considerably lower than usually reported in experiments using the Illumina instrument because we used very stringent criteria for base calling.

TABLE 1

| Safe-SeqS with Endogenous UIDs | | |
|---|---|---|
|  | Capture | Inverse PCR |
| Conventional Analysis | | |
| High quality bp | 106,958,863 | 1,041,346,645 |
| Mean high quality bp read depth | 38,620× | 2,085,600× |
| Mutations identified | 25,563 | 234,352 |
| Mutations/bp | 2.4E−04 | 2.3E−04 |
| Safe-SeqS Analysis | | |
| High quality bp | 106,958,863 | 1,041,346,645 |
| Mean high quality bp read depth | 38,620× | 2,085,600× |
| UID-families | 69,505 | 1,057 |
| Average # of members/UID-family | 40 | 21,688 |
| Median # of members/UID-family | 19 | 4 |
| Super-mutants identified | 8 | 0 |
| Super-mutants/bp | 3.5E−06 | 0.0 |

With Safe-SeqS analysis of the same data, we determined that 69,505 original template molecules were assessed in this experiment (i.e., 69,505 UID-families, with an average of 40 members per family, were identified, Table 1). All of the polymorphic variants identified by conventional analysis were also identified by Safe-SeqS. However, only 8 super-mutants were observed among these families, corresponding to $3.5 \times 10^{-6}$ mutations/bp. Thus Safe-SeqS decreased the presumptive sequencing errors by at least 70-fold.

Safe-SeqS analysis can also determine which strand of a template is mutated, thus an additional criteria for calling mutations could require that the mutation appears in only one or in both strands of the originally double stranded template. Massively parallel sequencers are able to obtain sequence information from both ends of a template in two sequential reads. (This type of sequencing experiment is called a "paired end" run on the Illumina platform, but similar experiments can be done on other sequencing platforms where they may be called by another name.) The two strands of a double stranded template can be differentiated by the observed orientation of the sequences and the order in which they appear when sequence information is obtained from both ends. For example, a UID strand pair could consist of the following two groups of sequences when each end of a template is sequenced in sequential reads: 1) A sequence in the sense orientation that begins at position 100 of chromosome 2 in the first read followed by a sequence in the antisense orientation that begins at position 400 of chromosome 2 in the second read; and 2) A sequence in the antisense orientation that begins at position 400 of chromosome 2 in the first read followed by a sequence in the sense orientation that begins at position 100 of chromosome 2 in the second read. In the capture experiment described above, 42,222 of 69,505 UIDs (representing 21,111 original double stranded molecules) in the region of interest represented UID strand pairs. These 42,222 UIDs encompassed 1,417,838 bases in the region of interest. When allowing a mutation to only occur within UID strand pairs (whether in one or both strands), two super-mutants were observed, yielding a mutation rate of $1.4 \times 10^{-6}$ super-mutants/bp. When requiring that a mutation occur in only one strand of a UID strand pair, only one super-mutant was observed, yielding a mutation rate of $7.1 \times 10^{-7}$ super-mutants/bp. When requiring that a mutation occur in both strands of a UID strand pair, only one super-mutant was observed, yielding a mutation rate of $7.1 \times 10^{-7}$ super-mutants/bp. Thus, requiring that mutations occur in only one or in both strands of templates can further increase the specificity of Safe-SeqS.

A strategy employing endogenous UIDs was also used to reduce false positive mutations upon deep sequencing of a single region of interest. In this case, a library prepared as described above from ~1,750 normal cells was used as template for inverse PCR employing primers complementary to a gene of interest, so the PCR products could be directly used for sequencing (FIG. 5). With conventional analysis, an average of $2.3 \times 10^{-4}$ mutations/bp were observed, similar to that observed in the capture experiment (Table 1). Given that only 1,057 independent molecules from normal cells were assessed in this experiment, as determined through Safe-SeqS analysis, all mutations observed with conventional analysis likely represented false positives (Table 1). With Safe-SeqS analysis of the same data, no super-mutants were identified at any position.

EXAMPLE 2

Exogenous UIDs

Though the results described above show that Safe-SeqS can increase the reliability of massively parallel sequencing, the number of different molecules that can be examined using endogenous UIDs is limited. For fragments sheared to an average size of 150 bp (range 125-175), 36 base paired-end sequencing can evaluate a maximum of ~7,200 different molecules containing a specific mutation (2 reads×2 orientations×36 bases/read×50 base variation on either end of the fragment). In practice, the actual number of UIDs is smaller because the shearing process is not entirely random.

Figure 3:
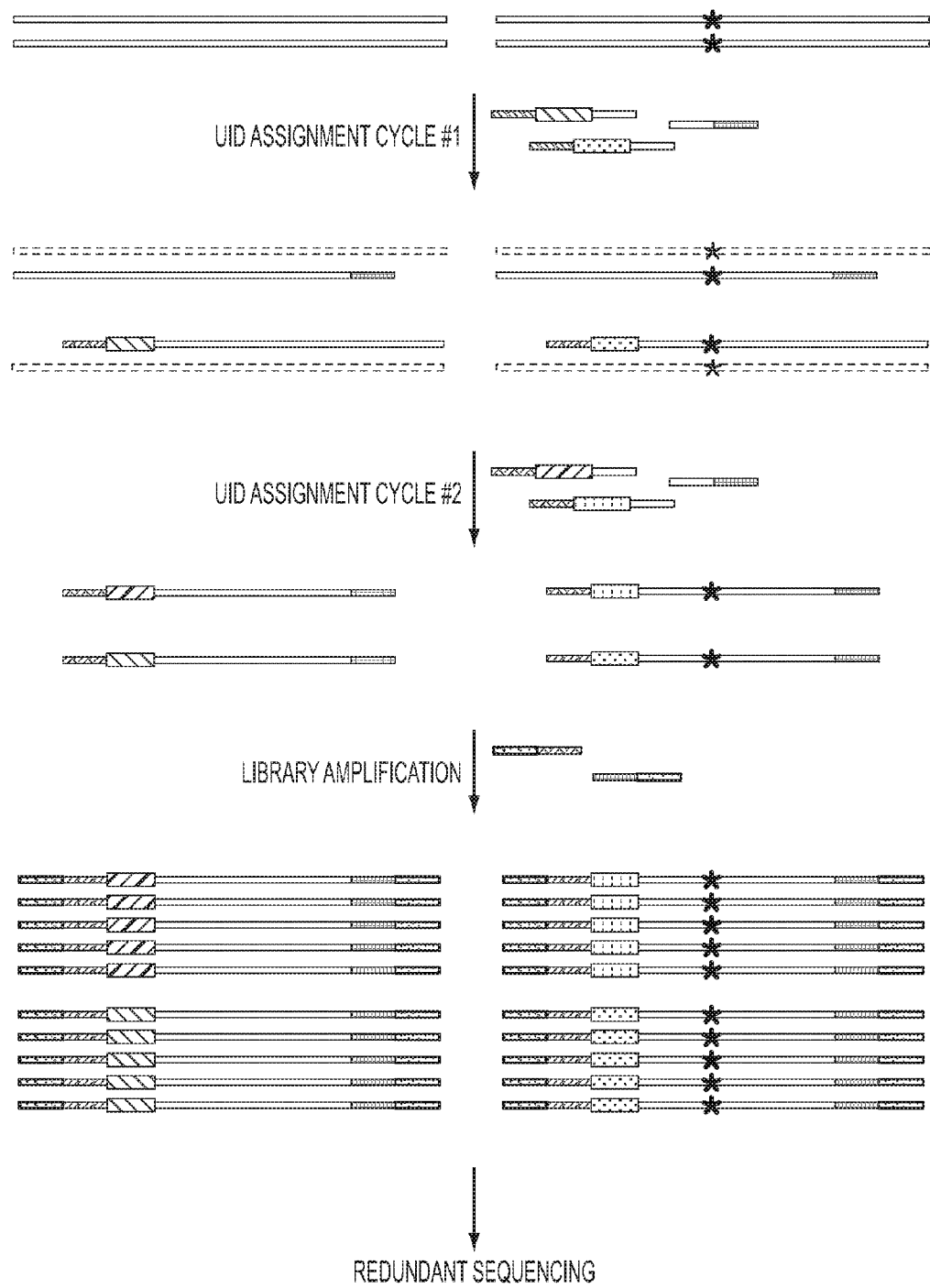
FIG. 3. Safe-SeqS with Exogenous UIDs. DNA (sheared or unsheared) is amplified with a set of gene-specific primers. One of the primers has a random DNA sequence (e.g., a set of 14 N's) that forms the unique identifier (UID; variously shaded bars), located 5' to its gene-specific sequence, and both have sequences that permit universal amplification in the next step (earth hatched and cross hatched bars). Two UID assignment cycles produce two fragments—each with a different UID—from each double-stranded template molecule, as shown. Subsequent PCR with universal primers, which also contain "grafting" sequences (adhesive filled and light stippled bars), produces UID-families which are directly sequenced. Super-mutants are defined as in the legend to FIG. 1.

To make more efficient use of the original templates, we developed a Safe-SeqS strategy that employed a minimum number of enzymatic steps. This strategy also permitted the use of degraded or damaged DNA, such as found in clinical specimens or after bisulfite-treatment for the examination of cytosine methylation (45). As depicted in FIG. 3, this strategy employs two sets of PCR primers. The first set is synthesized with standard phosphoramidite precursors and contained sequences complementary to the gene of interest on the 3' end and different tails at the 5' ends of both the forward and reverse primers. The different tails allowed universal amplification in the next step. Finally, there was a stretch of 12 to 14 random nucleotides between the tail and the sequence-specific nucleotides in the forward primer (40). The random nucleotides form the UIDs. An equivalent way to assign UIDs to fragments, not used in this study, would employ 10,000 forward primers and 10,000 reverse primers synthesized on a microarray. Each of these 20,000 primers would have gene-specific primers at their 3'-ends and one of 10,000 specific, predetermined, non-overlapping UID sequences at their 5'-ends, allowing for $10^8$ (i.e., $[10^4]^2$) possible UID combinations. In either case, two cycles of PCR are performed with the primers and a high-fidelity polymerase, producing a uniquely tagged, double-stranded DNA fragment from each of the two strands of each original template molecule (FIG. 3). The residual, unused UID assignment primers are removed by digestion with a single-strand specific exonuclease, without further purification, and two new primers are added. Alternatively or in addition to such digestion, one can use a silica column that selectively retains larger-sized fragments or one can use solid phase reversible immobilization (SPRI) beads under conditions that selectively retain larger fragments to eliminate smaller, non-specific, amplification artifacts. This purification may potentially help in reducing primer-dimer accumulation in later steps. The new primers, complementary to the tails introduced in the UID assignment cycles, contain grafting sequences at their 5' ends, permitting solid-phase amplification on the Illumina instrument, and phosphorothioate residues at their 3' ends to make them resistant to any remaining exonuclease. Following 25 additional cycles of PCR, the products are loaded on the Illumina instrument. As shown below, this strategy allowed us to evaluate the majority of input fragments and was used for several illustrative experiments.

EXAMPLE 3

Analysis of DNA Polymerase Fidelity

Measurement of the error rates of DNA polymerases is essential for their characterization and dictates the situations in which these enzymes can be used. We chose to measure the error rate of Phusion polymerase, as this polymerase has one of the lowest reported error frequencies of any commercially available enzyme and therefore poses a particular challenge for an in vitro-based approach. We first amplified a single human DNA template molecule, comprising a segment of an arbitrarily chosen human gene, through 19 rounds of PCR. The PCR products from these amplifications, in their entirety, were used as templates for Safe-SeqS as described in FIG. 3. In seven independent experiments of this type, the number of UID-families identified by sequencing was 624,678±421,274, which is consistent with an amplification efficiency of 92±9.6% per round of PCR.

The error rate of Phusion polymerase, estimated through cloning of PCR products encoding β-galactosidase in plasmid vectors and transformation into bacteria, is reported by the manufacturer to be $4.4 \times 10^{-7}$ errors/bp/PCR cycle. Even with very high stringency base-calling, conventional analysis of the Illumina sequencing data revealed an apparent error rate of $9.1 \times 10^{-6}$ errors/bp/PCR cycle, more than an order of magnitude higher than the reported Phusion polymerase error rate (Table 2A). In contrast, Safe-SeqS of the same data revealed an error rate of $4.5 \times 10^{-7}$ errors/bp/PM cycle, nearly identical to that measured for Phusion polymerase in biological assays (Table 2A). The vast majority (>99%) of these errors were single base substitutions (Table 3A), consistent with previous data on the mutation spectra created by other prokaryotic DNA polymerases (15, 46, 47).

TABLE 2A-2C

Safe-SeqS with Exogenous UIDs

| | Mean | Standard Deviation |
|---|---|---|
| 2A. Polymerase Fidelity | | |
| Conventional analysis of 7 replicates | | |
| High quality bp | 996,855,791 | 64,030,757 |
| Total mutations identified | 198,638 | 22,515 |
| Mutations/bp | 2.0E−04 | 1.7E−05 |
| Calculated Phusion Error Rate (errors/bp/cycle) | 9.1E−06 | 7.7E−07 |
| Safe-SeqS analysis of 7 replicates | | |
| High quality bp | 996,855,791 | 64,030,757 |
| UID-families | 624,678 | 421,274 |
| Members/UID-family | 107 | 122 |
| Total super-mutants identified | 197 | 143 |
| Super-mutants/bp | 9.9E−06 | 2.3E−06 |
| Calculated Phusion Error Rate (errors/bp/cycle) | 4.5E−07 | 1.0E−07 |
| 2B. CTNNB1 mutations in DNA from normal human cells | | |
| Conventional analysis of 3 individuals | | |
| High quality bp | 559,334,774 | 66,600,749 |
| Total mutations identified | 118,488 | 11,357 |
| Mutations/bp | 2.1E−04 | 1.6E−05 |
| Safe-SeqS analysis of 3 individuals | | |
| High quality bp | 559,334,774 | 66,600,749 |
| UID-families | 374,553 | 263,105 |
| Members/UID-family | 68 | 38 |
| Total super-mutants identified | 99 | 78 |
| Super-mutants/bp | 9.0E−06 | 3.1E−06 |
| 2C. Mitochondrial mutations in DNA from normal human cells | | |
| Conventional analysis of 7 individuals | | |
| High quality bp | 147,673,456 | 54,308,546 |
| Total mutations identified | 30,599 | 12,970 |
| Mutations/bp | 2.1E−04 | 9.4E−05 |
| Safe-SeqS analysis of 7 individuals | | |
| High quality bp | 147,673,456 | 54,308,546 |
| UID-families | 515,600 | 89,985 |
| Members/UID-family | 15 | 6 |
| Total super-mutants identified | 135 | 61 |
| Super-mutants/bp | 1.4E−05 | 6.8E−06 |

TABLE 3A-C

Fraction of Single Base Substitutions, Insertions, and Deletions with Exogenous UIDs

| | Mean | Standard Deviation |
|---|---|---|
| 3A. Polymerase Fidelity | | |
| Conventional analysis of 7 replicates | | |
| Total mutations identified | 198,638 | 22,515 |
| Fraction of mutations represented by single base substitutions | 99% | 0% |
| Fraction of mutations represented by deletions | 1% | 0% |
| Fraction of mutations represented by insertions | 0% | 0% |
| Safe-SeqS analysis of 7 replicates | | |
| Total super-mutants identified | 197 | 143 |
| Fraction of super-mutants represented by single base substitutions | 99% | 2% |
| Fraction of super-mutants represented by deletions | 1% | 2% |
| Fraction of super-mutants represented by insertions | 0% | 0% |
| 3B. CTNNB1 mutations in DNA from normal human cells | | |
| Conventional analysis of 3 individuals | | |
| Total mutations identified | 118,488 | 11,357 |
| Fraction of mutations represented by single base substitutions | 97% | 0% |
| Fraction of mutations represented by deletions | 3% | 0% |
| Fraction of mutations represented by insertions | 0% | 0% |
| Safe-SeqS analysis of 3 individuals | | |
| Total super-mutants identified | 99 | 78 |
| Fraction of super-mutants represented by single base substitutions | 100% | 1% |
| Fraction of super-mutants represented by deletions | 0% | 1% |
| Fraction of super-mutants represented by insertions | 0% | 0% |
| 3C. Mitochondrial mutations in DNA from normal human cells | | |
| Conventional analysis of 7 individuals | | |
| Total mutations identified | 30,599 | 12,970 |
| Fraction of mutations represented by single base substitutions | 98% | 1% |
| Fraction of mutations represented by deletions | 2% | 1% |
| Fraction of mutations represented by insertions | 0% | 0% |
| Safe-SeqS analysis of 7 individuals | | |
| Total super-mutants identified | 135 | 61 |
| Fraction of super-mutants represented by single base substitutions | 99% | 1% |
| Fraction of super-mutants represented by deletions | 1% | 1% |
| Fraction of super-mutants represented by insertions | 0% | 0% |

Safe-SeqS also allowed a determination of the total number of distinct mutational events and an estimation of PCR cycle in which the mutation occurred. There were 19 cycles of PCR performed in wells containing a single template molecule in these experiments. If a polymerase error occurred in cycle 19, there would be only one super-mutant produced (from the strand containing the mutation). If the error occurred in cycle 18 there should be two super-mutants (derived from the mutant strands produced in cycle 19), etc. Accordingly, the cycle in which the error occurred is related to the number of super-mutants containing that error. The data from seven independent experiments demonstrate a relatively consistent number of observed total polymerase errors ($2.2 \pm 1.1 \times 10^{-6}$ distinct mutations/bp), in good agreement with the expected number of observations from simulations ($1.5 \pm 0.21 \times 10^{-6}$ distinct mutations/bp). The data also show a highly variable timing of occurrence of polymerase errors among experiments (Table 4), as predicted from classic fluctuation analysis (1). This kind of information is difficult to derive using conventional analysis of the same next-generation sequencing data, in part because of the prohibitively high apparent mutation rate noted above.

TABLE 4A-4G

Observed and Expected Number of Errors Generated by Phusion Polymerase

| | Observed | Expected (mean ± SD)* |
|---|---|---|
| 4A. Experiment 1 | | |
| Mutations represented by 1 super-mutant | 10 | 19 ± 3.7 |
| Mutations represented by 2 super-mutants | 8 | 5.8 ± 7.3 |
| Mutations represented by 3 super-mutants | 4 | 1.3 ± 1.1 |
| Mutations represented by 4 super-mutants | 4 | 1.8 ± 1.3 |
| Mutations represented by 5 super-mutants | 2 | 0.61 ± 0.75 |
| Mutations represented by 6 super-mutants | 2 | 0.22 ± 0.44 |
| Mutations represented by 7 super-mutants | 0 | 0.01 ± 0.10 |
| Mutations represented by 8 super-mutants | 0 | 0.87 ± 0.86 |
| Mutations represented by 9 super-mutants | 2 | 0.28 ± 0.51 |
| Mutations represented by 10 super-mutants | 0 | 0.14 ± 0.38 |
| Mutations represented by >10 super-mutants | 3 | 1.5 ± 2.7 |
| Distinct mutations | 35 | 32 ± 4.2 |
| 4B. Experiment 2 | | |
| Mutations represented by 1 super-mutant | 19 | 23 ± 4.1 |
| Mutations represented by 2 super-mutants | 5 | 9.5 ± 2.8 |
| Mutations represented by 3 super-mutants | 4 | 2.7 ± 1.6 |
| Mutations represented by 4 super-mutants | 7 | 2.7 ± 1.7 |
| Mutations represented by 5 super-mutants | 2 | 0.88 ± 0.94 |
| Mutations represented by 6 super-mutants | 1 | 0.40 ± 0.60 |
| Mutations represented by 7 super-mutants | 3 | 0.16 ± 0.42 |
| Mutations represented by 8 super-mutants | 1 | 0.99 ± 1.0 |
| Mutations represented by 9 super-mutants | 1 | 0.39 ± 0.68 |
| Mutations represented by 10 super-mutants | 0 | 0.17 ± 0.43 |
| Mutations represented by >10 super-mutants | 9 | 1.8 ± 3.4 |
| Distinct mutations | 52 | 43 ± 5.1 |
| 4C. Experiment 3 | | |
| Mutations represented by 1 super-mutant | 7 | 17 ± 3.4 |
| Mutations represented by 2 super-mutants | 9 | 5.4 ± 2.0 |
| Mutations represented by 3 super-mutants | 4 | 1.2 ± 1.1 |
| Mutations represented by 4 super-mutants | 4 | 1.7 ± 1.4 |
| Mutations represented by 5 super-mutants | 2 | 0.50 ± 0.70 |
| Mutations represented by 6 super-mutants | 0 | 0.17 ± 0.45 |
| Mutations represented by 7 super-mutants | 1 | 0.03 ± 0.17 |
| Mutations represented by 8 super-mutants | 0 | 0.59 ± 0.74 |
| Mutations represented by 9 super-mutants | 0 | 0.24 ± 0.50 |
| Mutations represented by 10 super-mutants | 1 | 0.07 ± 0.29 |
| Mutations represented by >10 super-mutants | 5 | 1.5 ± 2.6 |
| Distinct mutations | 33 | 28 ± 3.7 |
| 4D. Experiment 4 | | |
| Mutations represented by 1 super-mutant | 7 | 15 ± 3.7 |
| Mutations represented by 2 super-mutants | 8 | 4.1 ± 1.7 |
| Mutations represented by 3 super-mutants | 2 | 0.70 ± 0.74 |
| Mutations represented by 4 super-mutants | 1 | 1.5 ± 1.3 |
| Mutations represented by 5 super-mutants | 3 | 0.21 ± 0.52 |
| Mutations represented by 6 super-mutants | 2 | 0.08 ± 0.27 |
| Mutations represented by 7 super-mutants | 1 | 0.0 ± 0.0 |
| Mutations represented by 8 super-mutants | 2 | 0.65 ± 0.77 |
| Mutations represented by 9 super-mutants | 2 | 0.17 ± 0.43 |
| Mutations represented by 10 super-mutants | 0 | 0.05 ± 0.22 |
| Mutations represented by >10 super-mutants | 1 | 0.92 ± 2.1 |
| Distinct mutations | 29 | 23 ± 3.2 |
| 4E. Experiment 5 | | |
| Mutations represented by 1 super-mutant | 9 | 23 ± 4.1 |
| Mutations represented by 2 super-mutants | 6 | 9.5 ± 2.8 |
| Mutations represented by 3 super-mutants | 5 | 2.7 ± 1.6 |
| Mutations represented by 4 super-mutants | 3 | 2.7 ± 1.7 |
| Mutations represented by 5 super-mutants | 6 | 0.88 ± 0.94 |
| Mutations represented by 6 super-mutants | 2 | 0.40 ± 0.60 |
| Mutations represented by 7 super-mutants | 1 | 0.16 ± 0.42 |
| Mutations represented by 8 super-mutants | 2 | 0.99 ± 1.0 |
| Mutations represented by 9 super-mutants | 2 | 0.39 ± 0.68 |
| Mutations represented by 10 super-mutants | 3 | 0.17 ± 0.43 |
| Mutations represented by >10 super-mutants | 7 | 1.8 ± 3.4 |
| Distinct mutations | 46 | 43 ± 5.1 |
| 4F. Experiment 6 | | |
| Mutations represented by 1 super-mutant | 4 | 6.7 ± 2.8 |
| Mutations represented by 2 super-mutants | 7 | 1.5 ± 1.2 |
| Mutations represented by 3 super-mutants | 1 | 0.10 ± 0.33 |
| Mutations represented by 4 super-mutants | 2 | 0.60 ± 0.82 |
| Mutations represented by 5 super-mutants | 0 | 0.07 ± 0.26 |
| Mutations represented by 6 super-mutants | 0 | 0.01 ± 0.10 |
| Mutations represented by 7 super-mutants | 1 | 0.0 ± 0.0 |
| Mutations represented by 8 super-mutants | 1 | 0.39 ± 0.60 |
| Mutations represented by 9 super-mutants | 0 | 0.01 ± 0.10 |
| Mutations represented by 10 super-mutants | 0 | 0.0 ± 0.0 |
| Mutations represented by >10 super-mutants | 2 | 0.50 ± 1.1 |
| Distinct mutations | 18 | 9.9 ± 1.4 |
| 4G. Experiment 7 | | |
| Mutations represented by 1 super-mutant | 8 | 2.9 ± 1.6 |
| Mutations represented by 2 super-mutants | 2 | 0.61 ± 0.79 |
| Mutations represented by 3 super-mutants | 0 | 0.04 ± 0.24 |
| Mutations represented by 4 super-mutants | 0 | 0.41 ± 0.59 |
| Mutations represented by 5 super-mutants | 1 | 0.01 ± 0.10 |
| Mutations represented by 6 super-mutants | 0 | 0.0 ± 0.0 |
| Mutations represented by 7 super-mutants | 0 | 0.0 ± 0.0 |
| Mutations represented by 8 super-mutants | 0 | 0.14 ± 0.35 |
| Mutations represented by 9 super-mutants | 0 | 0.01 ± 0.10 |
| Mutations represented by 10 super-mutants | 0 | 0.0 ± 0.0 |
| Mutations represented by >10 super-mutants | 0 | 0.32 ± 0.93 |
| Distinct mutations | 11 | 4.5 ± 0.62 |

*See SI Text for details of the simulations

EXAMPLE 4

Analysis of Oligonucleotide Composition

A small number of mistakes during the synthesis of oligonucleotides from phoshoramidite precursors are tolerable for most applications, such as routine PCR or cloning. However, for synthetic biology, wherein many oligonucleotides must be joined together, such mistakes present a major obstacle to success. Clever strategies for making the gene construction process more efficient have been devised (48, 49), but all such strategies would benefit from more accurate synthesis of the oligonucleotides themselves. Determining the number of errors in synthesized oligonucleotides is difficult because the fraction of oligonucleotides containing errors can be lower than the sensitivity of conventional next-generation sequencing analyses.

Figures 6A, 6B:
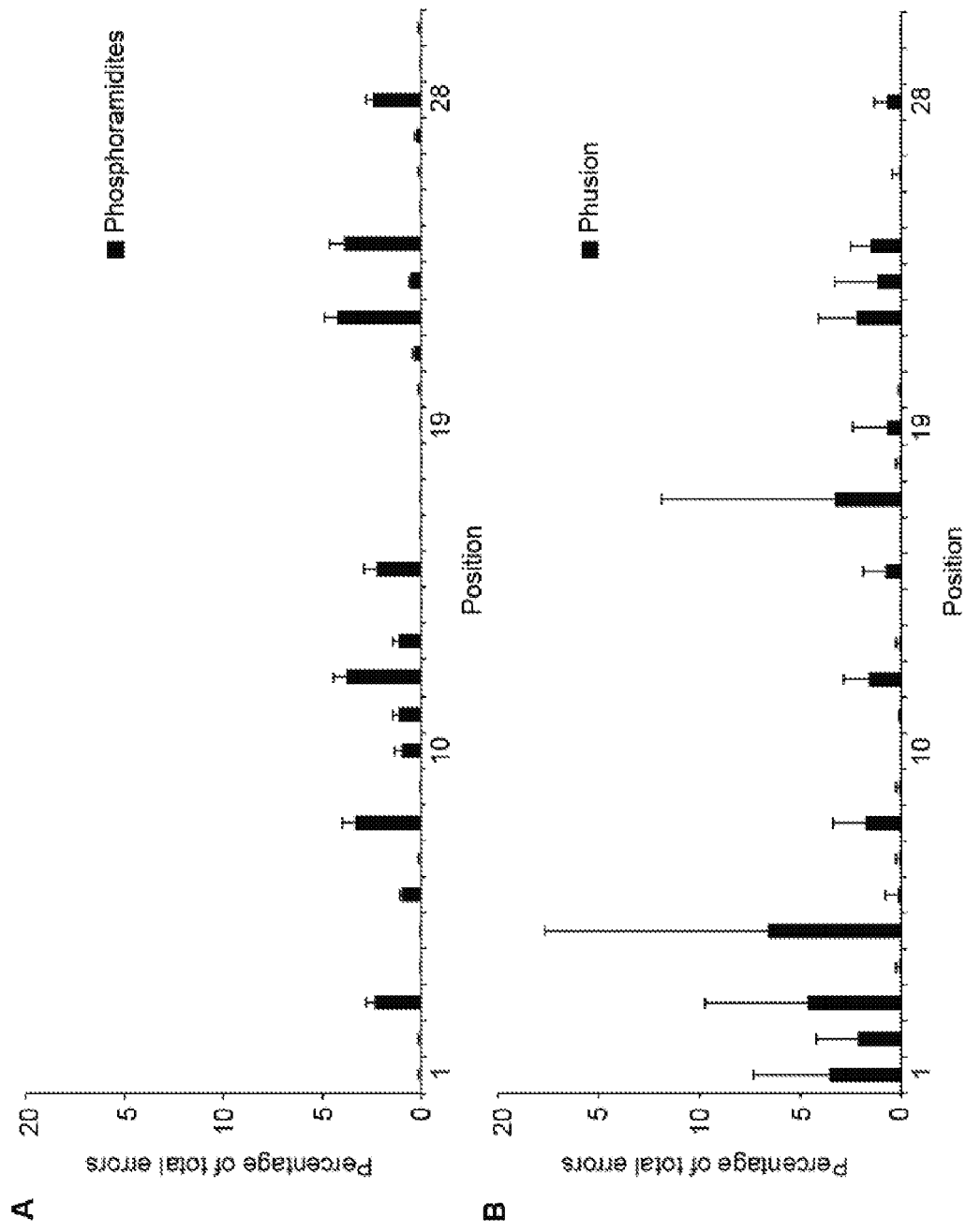
FIG. 6A-6B. Single base substitutions position vs. error frequency in oligonucleotides synthesized with phosphoramidites and Phusion. A representative portion of the same 31-base DNA fragment synthesized with phosphoramidites (FIG. 6A) or Phusion polymerase (FIG. 6B) was analyzed by Safe-SeqS. The means and standard deviations for seven independent experiments of each type are plotted. There was an average of 1,721±383 and 196±143 SBS super-mutants identified in the phosphoramidite-synthesized and Phusion-generated fragments, respectively. The y-axis indicates the fraction of the total errors at the indicated position. Note that the errors in the phosphoramidite-synthesized DNA fragment were consistent among the seven replicates, as would be expected if the errors were systematically introduced during the synthesis itself. In contrast, the errors in the Phusion-generated fragments appeared to be heterogeneous among samples, as expected from a stochastic process (Luria and Delbruck, *Genetics* 28: 491-511, 1943).

To determine whether Safe-SeqS could be used for this determination, we used standard phosphoramidite chemistry to synthesize an oligonucleotide containing 31 bases that were designed to be identical to that analyzed in the polymerase fidelity experiment described above. In the synthetic oligonucleotide, the 31 bases were surrounded by sequences complementary to primers that could be used for the UID assignment steps of Safe-SeqS (FIG. 3). By performing Safe-SeqS on ~300,000 oligonucleotides, we found that there were $8.9 \pm 0.28 \times 10^{-4}$ super-mutants/bp and that these errors occurred throughout the oligonucleotides (FIG. 6A). The oligonucleotides contained a large number of insertion and deletion errors, representing $8.2 \pm 0.63\%$ and $25 \pm 1.5\%$ of the total super-mutants, respectively, importantly, both the position and nature of the errors were highly reproducible among seven independent replicates of this experiment performed on the same batch of oligonucleotides (FIG. 6A). This nature and distribution of errors had little in common with that of the errors produced by Phusion polymerase (FIG. 6B and Table 5), which were distributed in the expected stochastic pattern among replicate experiments.

The number of errors in the oligonucleotides synthesized with phosphoramidites was ~60 times higher than in the equivalent products synthesized by Phusion polymerase. These data, in toto, indicate that the vast majority of errors in the former were generated during their synthesis rather than during the Safe-SeqS procedure.

TABLE 5

Phosphoramidite- vs Phusion-Synthesized DNA: Transitions vs Transversions Comparison

|  | Exp. 1 | Exp. 2 | Exp. 3 | Exp. 4 | Exp. 5 | Exp. 6 | Exp. 7 | Average | Standard Deviation |
|---|---|---|---|---|---|---|---|---|---|
| Phosphoramidites |  |  |  |  |  |  |  |  |  |
| Transition super-mutants: | 496 | 509 | 471 | 396 | 323 | 273 | 470 | 420 | 92 |
| Transversion super-mutants: | 1494 | 1499 | 1521 | 1154 | 944 | 907 | 1626 | 1306 | 298 |
| p-value* | 3.4E−05 |  |  |  |  |  |  |  |  |
| Phusion |  |  |  |  |  |  |  |  |  |
| Transition super-mutants: | 63 | 275 | 127 | 5 | 87 | 182 | 103 | 120 | 87 |
| Transversion super-mutants: | 14 | 124 | 77 | 12 | 57 | 191 | 63 | 77 | 63 |
| p-value* | 0.08 |  |  |  |  |  |  |  |  |

*p-values were calculated using a two-tailed paired t-test

Does Safe-SeqS preserve the ratio of mutant:normal sequences in the original templates'? To address this question, we synthesized two 31-base oligonucleotides of identical sequence with the exception of nt 15 (50:50 C/G instead of T) and mixed them at nominal mutant/normal fractions of 3.3% and 0.33%. Through Safe-SeqS analysis of the oligonucleotide mixtures, we found that the ratios were 2.8% and 0.27%, respectively. We conclude that the UID assignment and amplification procedures used in Safe-SeqS do not greatly alter the proportion of variant sequences and thereby provide a reliable estimate of that proportion when unknown. This conclusion is also supported by the reproducibility of variant fractions when analyzed in independent Safe-SeqS experiments (FIG. 6A).

EXAMPLE 5

Analysis of DNA Sequences from Normal Human Cells

Figure 4A:
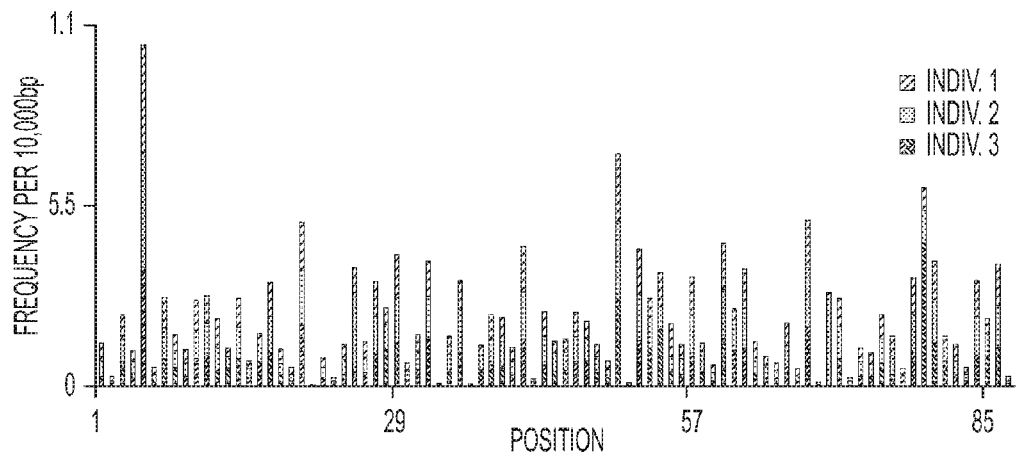
FIGS. 4A-4B. Single Base Substitutions Identified by Conventional and Safe-SeqS Analysis. The exogenous UID strategy depicted in FIG. 3 was used to produce PCR fragments from the CTNNB1 gene of three normal, unrelated individuals. Each position represents one of 87 possible single base substitutions (3 possible substitutions/base×29 bases analyzed). These fragments were sequenced on an Illumina GA IIx instrument and analyzed in the conventional manner (FIG. 4A) or with Safe-SeqS (FIG. 4B). Safe-SeqS results are displayed on the same scale as conventional analysis for direct comparison; the inset is a magnified view. Note that most of the variants identified by conventional analysis are likely to represent sequencing errors, as indicated by their high frequency relative to Safe-SeqS and their consistency among unrelated samples.
Figure 4B:
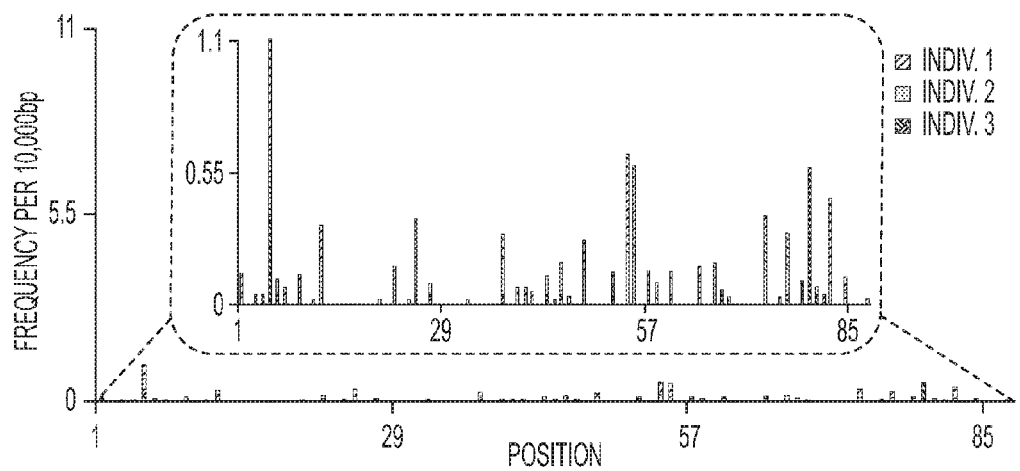
Figure 7:
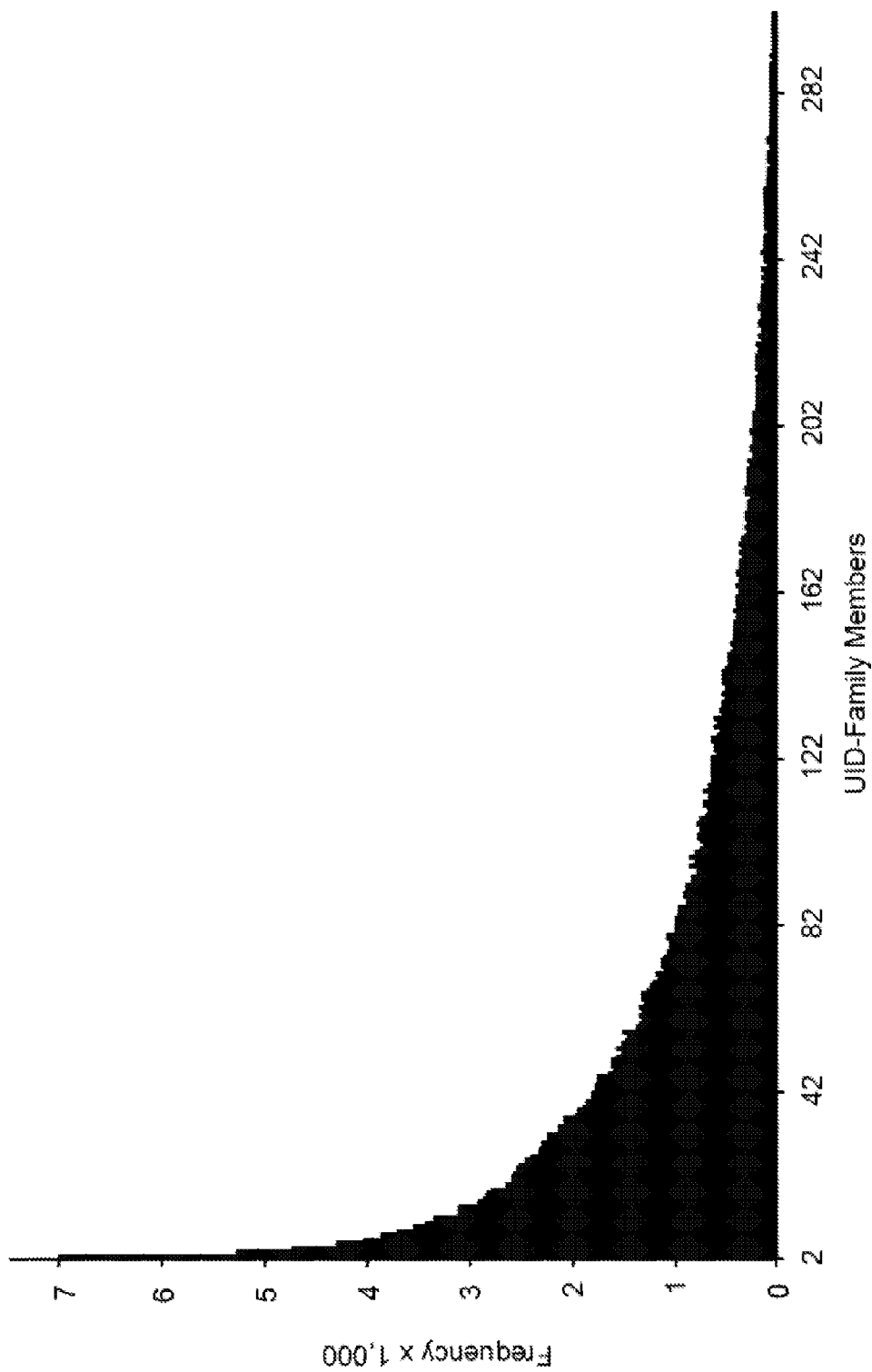
FIG. 7. UID-family member distribution. The exogenous UID strategy depicted in FIG. 3 was used to produce PCR fragments from a region of CTNNB1 from three normal, unrelated individuals (Table 2B); a representative example of the UID-families with ≤300 members (99% of total UID-families) generated from one individual is shown. The y-axis indicates the number of different UID-families that contained the number of family members shown on the x-axis.

The exogenous TAD strategy (FIG. 3) was then used to determine the prevalence of rare mutations in a small region of the CTNNB1 gene from ~100,000 normal human cells from three unrelated individuals. Through comparison with the number of UID-families obtained in the Safe-SeqS experiments (Table 2B), we calculated that the majority (78±9.8%) of the input fragments were converted into UID-families. There was an average of 68 members/UID-family, easily fulfilling the required redundancy for Safe-SeqS (FIG. 7). Conventional analysis of the Illumina sequencing data revealed an average of 118,488±11,357 mutations among the ~560 Mb of sequence analyzed per sample, corresponding to an apparent mutation prevalence of $2.1\pm0.16\times10^{-4}$ mutations/bp (Table 2B). Only an average of 99±78 super-mutants were observed in the Safe-SeqS analysis. The vast majority (>99%) of super-mutants were single base substitutions and the calculated mutation rate was $9.0\pm3.1\times10^{-6}$ mutations/bp (Table 3B). Safe-SeqS thereby reduced the apparent frequency of mutations in genomic DNA by at least 24-fold (FIG. 4).

One possible strategy to increase the specificity of Safe-SeqS is to perform the library amplification (and possibly the UID assignment cycles) in multiple wells. This can be accomplished in as few as 2 or as many as 384 wells using standard PCR plates, or scaled up to many more wells when using a microfluidic device (thousands to millions). When performed this way, indexing sequences can be introduced into the templates that are unique to the wells in which the template is amplified. Rare mutations, thus, should give rise to two super-mutants (i.e., one from each strand), both with the same well index sequence. When performing Safe-SeqS with exogenous UIDs on the CTNNB1 templates described above and diluted into 10 wells (each well yielding templates amplified with a different index sequence), the mutation rate was further reduced from $9.0\pm3.1\times10^{-6}$ to $3.7\pm1.2\times10^{-6}$ super-mutants/bp. Thus, analyzing templates in multiple compartments—in a manner that yields differentially encoded templates based on the compartment in which templates were amplified—may be an additional strategy to increase the specificity of Safe-SeqS.

EXAMPLE 6

Analysis of DNA Sequences from Mitochondrial DNA

We applied the identical strategy to a short segment of mitochondrial DNA in ~1,000 cells from each of seven unrelated individuals. Conventional analysis of the Illumina sequencing libraries produced with the Safe-SeqS procedure (FIG. 3) revealed an average of 30,599±12,970 mutations among the ~150 Mb of sequence analyzed per sample, corresponding to an apparent mutation prevalence of $2.1\pm0.94\times10^{-4}$ mutations/bp (Table 2C). Only 135±61 super-mutants were observed in the Safe-SeqS analysis. As with the CTNNB1 gene, the vast majority of mutations were single base substitutions, though occasional single base deletions were also observed (Table 3C). The calculated mutation rate in the analyzed segment of mtDNA was $1.4\pm0.68\times10^{-5}$ mutations/bp (Table 2C). Thus, Safe-SeqS thereby reduced the apparent frequency of mutations in genomic DNA by at least 15-fold.

EXAMPLE 7

Materials and Methods

Endogenous UIDs.
Genomic DNA from human pancreas or cultured lymphoblastoid cells was prepared using Qiagen kits. The pancreas DNA was used for the capture experiment and the lymphoblastoid cells were used for the inverse PCR experiment. DNA was quantified by optical absorbance and with qPCR. DNA was fragmented to an average size of ~200 bp by acoustic shearing (Covaris), then end-repaired, A-tailed, and ligated to Y-shaped adapters according to standard Illumina protocols. The ends of each template molecule provide endogenous UIDs corresponding to their chromosomal positions. After PCR-mediated amplification of the libraries with primer sequences within the adapters, DNA was captured (1) with a filter containing 2,594 nt corresponding to six cancer genes. After capture, 18 cycles of PCR were performed to ensure sufficient amounts of template for sequencing on an Illumina GA IIx instrument.

For the inverse PCR experiments (FIG. 5), we ligated custom adapters (IDT, Table 6) instead of standard Y-shaped Illumina adapters to sheared cellular DNA. These adapters retained the region complementary to the universal sequencing primer but lacked the grafting sequences required for hybridization to the Illumina GA IIx flow cell. The ligated DNA was diluted into 96 wells and the DNA in each column of 8 wells was amplified with a unique forward primer containing one of 12 index sequences at its 5' end plus a standard reverse primer (Table 6). Amplifications were performed using Phusion HotStart I (NEB) in 50 uL reactions containing 1× Phusion HF buffer, 0.5 mM dNTPs, 0.5 uM each forward and reverse primer (both 5'-phosphorylated), and 1 U of Phusion polymerase. The following cycling conditions were used: one cycle of 98° C. for 30 s; and 16 cycles of 98° C. for 10 s, 65° C. for 30 s, and 72° C. for 30 s. All 96 reactions were pooled and then purified using a Qiagen MinElute PCR. Purification Kit (cat. no. 28004) and a QIAquick Gel Extraction kit (cat. no. 28704). To prepare the circular templates necessary for inverse PCR, DNA was diluted to ~1 ng/uL and ligated with T4 DNA Ligase (Enzymatics) for 30 min at room temperature in a 600 uL reaction containing 1×T4 DNA Ligation Buffer and 18,000 U of T4 DNA Ligase. The ligation reaction was purified using a Qiagen MinElute kit. Inverse PCR was performed using Phusion Hot Start I on 90 ng of circular template distributed in twelve 50 uL reactions, each containing 1× Phusion HF Buffer, 0.25 mM dNTPs, 0.50 uM each of KRAS forward and reverse primers (Table 6) and 1 U of Phusion polymerase. The KRAS-specific primers both contained grafting sequences for hybridization to the Illumina GA IIx flow cell (Table 6). The following cycling conditions were used: one cycle of 98° C. for 2 min; and 37 cycles of 98° C. for 10 s, 61° C. for 15 s, and 72° C. for 10 s. The final purification was performed with a NucleoSpin Extract II kit (Macherey-Nagel) and eluted in 20 uL NE Buffer. The resulting DNA fragments contained UIDs composed of three sequences: two endogenous ones, represented by the two ends of the original sheared fragments plus the exogenous sequence introduced during the indexing amplification. As 12 exogenous sequences were used, this increased the number of distinct UIDs by 12-fold over that obtained without exogenous UIDs. This number could easily be increased by using a greater number of distinct primers.

TABLE 6

Oligonucleotides Used

| Font Legend: | Symbol Legend: |
|---|---|
| REGION COMPLEMENTARY TO TEMPLATES | /5Phos/ = 5' Phosphate |
| TEMPLATE-SPECIFIC UID SEQUENCE | * = Phosphorothioate linkage |
| UNIVERSAL SEQUENCE | |
| EXPERIMENT-SPECIFIC INDEX SEQUENCE ILLUMINA GRAFTING PRIMERS (FOR HYBRIDIZATION TO FLOW CELL) | |

Endogenous UIDs

Sequence (SEQ ID NO: 1-81, respectively)

| Capture | |
|---|---|
| Adapter - strand 1 | /5Phos/GATCGGAAGAGCGGTTCAGCAGGAATGCCGAG |
| Adapter - strand 2 | ACACTCTTTCCCTACACGACGCTCTTCCGAT*C*T |
| Whole Genome Amplification - for | AATGATACGGCGACCACCGAGATCTACACACACTCTTTCCCTACACGACGCTCTTCCGAT*C*T |
| Whole Genome Amplification - rev | CAAGCAGAAGACGGCATACGAGATCTCGGCATTCCTGCTGAACCGCTCTTCCGAT*C*T |
| Post-Capture Amplification - for | AATGATACGGCGACCACCGAGATCTACACACACTCTTTCCCTACACGACGCTCTTCCGAT*C*T |
| Post-Capture Amplification - rev | CAAGCAGAAGACGGCATACGAGATCTCGGCATTCCTGCTGAACCGCTCTTCCGAT*C*T |
| Sequencing Primer, Read 1 (Illumina; San Diego, CA) | ACACTCTTTCCCTACACGACGCTCTTCCGATCT |
| Sequencing Primer, Read 2 (Illumina; San Diego, CA) | CTCGGCATTCCTGCTGAACCGCTCTTCCGATCT |

TABLE 6-continued

Oligonucleotides Used

Inverse PCR

| | |
|---|---|
| Adapter - strand 1 | /5Phos/GATCGGAAGAGCGGTTCAGCAGGAATGCCGAG |
| Adapter - strand 2 | ACACTCTTTCCCTACACGACGCTCTTCCGAT*C*T |
| Whole Genome Amplification - for-1 | /5Phos/CGTGATACACTCTTTCCCTACACGACGCTCTTCCGAT*C*T |
| Whole Genome Amplification - for-2 | /5Phos/ACATCGACACTCTTTCCCTACACGACGCTCTTCCGAT*C*T |
| Whole Genome Amplification - for-3 | /5Phos/GCCTAAACACTCTTTCCCTACACGACGCTCTTCCGAT*C*T |
| Whole Genome Amplification - for-4 | /5Phos/TGGTCAACACTCTTTCCCTACACGACGCTCTTCCGAT*C*T |
| Whole Genome Amplification - for-5 | /5Phos/CACTGTACACTCTTTCCCTACACGACGCTCTTCCGAT*C*T |
| Whole Genome Amplification - for-6 | /5Phos/ATTGGCACACTCTTTCCCTACACGACGCTCTTCCGAT*C*T |
| Whole Genome Amplification - for-7 | /5Phos/GATCTGACACTCTTTCCCTACACGACGCTCTTCCGAT*C*T |
| Whole Genome Amplification - for-8 | /5Phos/TCAAGTACACTCTTTCCCTACACGACGCTCTTCCGAT*C*T |
| Whole Genome Amplification - for-9 | /5Phos/CTGATCACACTCTTTCCCTACACGACGCTCTTCCGAT*C*T |
| Whole Genome Amplification - for-10 | /5Phos/AAGCTAACACTCTTTCCCTACACGACGCTCTTCCGAT*C*T |
| Whole Genome Amplification - for-11 | /5Phos/GTAGCCACACTCTTTCCCTACACGACGCTCTTCCGAT*C*T |
| Whole Genome Amplification - for-12 | /5Phos/TACAAGACACTCTTTCCCTACACGACGCTCTTCCGAT*C*T |
| Whole Genome Amplification - rev | /5Phos/CTCGGCATTCCTGCTGAACCGCTCTTCCGAT*C*T |
| Inverse PCR - antisense | AATGATACGGCGACCACCGAGATCTACACCAGCAGGCCTTATAATAAAAATAATGA |
| Inverse PCR - for | CAAGCAGAAGACGGCATACGAGATTGACTGAATATAAACTTGTGGTAGTTG |
| Sequencing Primer 1 (to read internal sequences) | ACACTCTTTCCCTACACGACGCTCTTCCGATCT |
| Sequencing Primer 2 (to read internal sequences) | CTCGGCATTCCTGCTGAACCGCTCTTCCGATCT |
| Index Primer 1 (to read experiment indexes) | CGGAAGAGCGTCGTGTAGGGAAAGAGTGT |
| Index Primer 2 (to read experiment indexes) | CGGAAGAGCGGTTCAGCAGGAATGCCGAG |

Exogenous UIDs

Polymerase Fidelity

| | |
|---|---|
| Digital PCR Amplification - for | *GGTTACAGGCTCATGATGTAACC* |
| Digital PCR Amplification - rev | *GATACCAGCTTGGTAATGGCA* |
| UID Assignment Amplification - for | CGACGTAAAACGACGGCCAGTNNNNNNNNNNNNNN*GGTTACAGGCTCATGATGTAACC* |
| UID Assignment Amplification - rev | CACACAGGAAACAGCTATGACCATG*GATACCAGCTTGGTAATGGCA* |

TABLE 6-continued

Oligonucleotides Used

| | |
|---|---|
| Library Amplification - for-1 | AATGATACGGCGACCACCGAGATCTACACCGTGATCGACGTAAAACGACGGCCA*G*T |
| Library Amplification - for-2 | AATGATACGGCGACCACCGAGATCTACACACATCGCGACGTAAAACGACGGCCA*G*T |
| Library Amplification - for-3 | AATGATACGGCGACCACCGAGATCTACACGCCTAACGACGTAAAACGACGGCCA*G*T |
| Library Amplification - for-4 | AATGATACGGCGACCACCGAGATCTACACTGGTCACGACGTAAAACGACGGCCA*G*T |
| Library Amplification - for-5 | AATGATACGGCGACCACCGAGATCTACACCACTGTCGACGTAAAACGACGGCCA*G*T |
| Library Amplification - for-6 | AATGATACGGCGACCACCGAGATCTACACATTGGCCGACGTAAAACGACGGCCA*G*T |
| Library Amplification - for-7 | AATGATACGGCGACCACCGAGATCTACACGATCTGCGACGTAAAACGACGGCCA*G*T |
| Library Amplification - for-8 | AATGATACGGCGACCACCGAGATCTACACTCAAGTCGACGTAAAACGACGGCCA*G*T |
| Library Amplification - for-9 | AATGATACGGCGACCACCGAGATCTACACCTGATCCGACGTAAAACGACGGCCA*G*T |
| Library Amplification - for-10 | AATGATACGGCGACCACCGAGATCTACACAAGCTACGACGTAAAACGACGGCCA*G*T |
| Library Amplification-rev | CAAGCAGAAGACGGCATACGAGATCACACAGGAAACAGCTATGACCA*T*G |
| Sequencing Primer (to read UID and internal sequences) | CGACGTAAAACGACGGCCAGT |
| Index Primer (to read experiment indexes) | ACTGGCCGTCGTTTTACGTCG |
| CTNNB1 mutations in DNA from normal human cells | |
| UID Assignment Amplification - for | CGACGTAAAACGACGGCCAGT*NNNNNNNNNNNNNNNN*GCAGCAACAGTCTTACCTGGACT |
| UID Assignment Amplification - rev | CACACAGGAAACAGCTATGACCATGTCCACATCCTCTTCCTCAGGATT |
| Libraiy Amplification - for | AATGATACGGCGACCACCGAGATCTACACCGACGTAAAACGACGGCCA*G*T |
| Library Amplification - rev-1 | CAAGCAGAAGACGGCATACGAGATATCACGCACACAGGAAACAGCTATGACCA*T*G |
| Library Amplification - rev-2 | CAAGCAGAAGACGGCATACGAGATCGATGTCACACAGGAAACAGCTATGACCA*T*G |
| Library Amplification - rev-3 | CAAGCAGAAGACGGCATACGAGATTGACCACACACAGGAAACAGCTATGACCA*T*G |
| Library Amplification - rev-4 | CAAGCAGAAGACGGCATACGAGATGCCAATCACACAGGAAACAGCTATGACCA*T*G |
| Library Amplification - rev-5 | CAAGCAGAAGACGGCATACGAGATCAGATCCACACAGGAAACAGCTATGACCA*T*G |
| Library Amplification - rev-6 | CAAGCAGAAGACGGCATACGAGATACTTGACACACAGGAAACAGCTATGACCA*T*G |
| Library Amplification - rev-7 | CAAGCAGAAGACGGCATACGAGATGATCAGCACACAGGAAACAGCTATGACCA*T*G |
| Library Amplification - rev-8 | CAAGCAGAAGACGGCATACGAGATTAGCTTCACACAGGAAACAGCTATGACCA*T*G |
| Library Amplification - rev-9 | CAAGCAGAAGACGGCATACGAGATGGCTACCACACAGGAAACAGCTATGACCA*T*G |
| Library Amplification - rev-10 | CAAGCAGAAGACGGCATACGAGATCTTGTACACACAGGAAACAGCTATGACCA*T*G |

TABLE 6-continued

Oligonucleotides Used

| | |
|---|---|
| Sequencing Primer (to read UID and internal sequences) | CGACGTAAAACGACGGCCAGT |
| Index Primer (to read experiment indexes) | CATGGTCATAGCTGTTTCCTGTGTG |

Mitochondrial mutations in DNA from normal human cells

| | |
|---|---|
| UID Assignment Amplification - for | CGACGTAAAACGACGGCCAGTNNNNNNNNNNNNNNNNTTACCGAGAAAGCTCACAAGAA |
| UID Assignment Amplification - rev | CACACAGGAAACAGCTATGACCATGATGCTAAGGCGAGGATGAAA |
| Library Amplification - for-1 | AATGATACGGCGACCACCGAGATCTACACACATCGCGACGTAAAACGACGGCCA\*G\*T |
| Library Amplification - for-2 | AATGATACGGCGACCACCGAGATCTACACGCCTAACGACGTAAAACGACGGCCA\*G\*T |
| Library Amplification - for-3 | AATGATACGGCGACCACCGAGATCTACACTGGTCACGACGTAAAACGACGGCCA\*G\*T |
| Library Amplification - for-4 | AATGATACGGCGACCACCGAGATCTACACATTGGCCGACGTAAAACGACGGCCA\*G\*T |
| Library Amplification - for-5 | AATGATACGGCGACCACCGAGATCTACACGATCTGCGACGTAAAACGACGGCCA\*G\*T |
| Library Amplification - for-6 | AATGATACGGCGACCACCGAGATCTACACTCAAGTCGACGTAAAACGACGGCCA\*G\*T |
| Library Amplification - for-7 | AATGATACGGCGACCACCGAGATCTACACCTGATCCGACGTAAAACGACGGCCA\*G\*T |
| Library Amplification -rev | CAAGCAGAAGACGGCATACGAGATCACACAGGAAACAGCTATGACCA\*T\*G |
| Sequencing Primer 1 (to read UIDs) | CGACGTAAAACGACGGCCAGT |
| Sequencing Primer 2 (to read internal sequences) | CCTAATTCCCCCCATCCTTAC |
| Index Primer (to read experiment indexes) | ACTGGCCGTCGTTTTACGTCG |

Analysis of Phosphoramidite Oligonucleotide Composition

| | |
|---|---|
| Synthesized template, wt | GGTTACAGGCTCATGATGTAACCTCTGTGTCTTGGTG<u>T</u>AACTTTAAAACATATTTTGCCATTACCAAGCTGGTATC |
| Synthesized template, mut (S = 50/50 mix of C and G) | GGTTACAGGCTCATGATGTAACCTCTGTGTCTTGGTG<u>S</u>AACTTTAAAACATATTTTGCCATTACCAAGCTGGTATC |
| UID Assignment Amplification - for | ACACTCTTTCCCTACACGACGCTNNNNNNNNNNNNNNGGTGAGTCTGTGCAGGCAT |
| UID Assignment Amplification - rev | CTCGAGCACTGTCCTGACTGAGACGATACCAGCTTGGTAATGGCA |
| Library Amplification - for | AATGATACGGCGACCACCGAGATCTACACCGTGATACACTCTTTCCCTACACGACGC\*T\*C |
| Library Amplification - rev Sequencing Primer (to read UID and internal sequences) | CAAGCAGAAGACGGCATACGAGATCTCGAGCACTGTCCTGACTGAG\*A\*C ACACTCTTTCCCTACACGACGCTC |

Exogenous UIDs.

Genomic DNA from normal human colonic mucosae or blood lymphocytes was prepared using Qiagen kits. The DNA from colonic mucosae was used for the experiments on CTNNB1 and mitochondrial DNA, while the lymphocyte DNA was used for the experiments on CTNNB1 and on polymerase fidelity. DNA was quantified with Digital PCR (2) using primers that amplified single-copy genes from human cells (Analysis of Polymerase Fidelity and CTNNB1), qPCR (mitochondrial DNA), or by optical absorbance (oligonucleotides). Each strand of each template molecule was encoded with a 12 or 14 base UID using two cycles of amplicon-specific PCR, as described in the text and FIG. 3. The amplicon-specific primers both contained universal tag sequences at their 5' ends for a later amplification step. The UIDs constituted 12 or 14 random nucleotide sequences appended to the 5' end of the forward amplicon-specific primers (Table 6). These primers can generate 16.8 and 268 million distinct UIDs, respectively. It is important that the number of distinct UIDs greatly exceed the number of original template molecules to minimize the probability that two different original templates acquired the same UID. The UID assignment PCR cycles included Phusion Hot Start II (NEB) in a 45 uL reaction containing 1× Phusion HF buffer, 0.25 mM dNTPs, 0.5 uM each forward (containing 12-14 Ns) and reverse primers, and 2 U of Phusion polymerase. To keep the final template concentrations <1.5 ng/uL, multiple wells were used to create some libraries. The following cycling conditions were employed: one incubation of 98° C. for 30 s (to activate the Phusion Hot Start II); and two cycles of 98° C. for 10 s, 61° C. for 120 s, and 72° C. for 10 s. To ensure complete removal of the first round primers, each well was digested with 60 U of a single strand DNA specific nuclease (Exonuclease-I; Enzymatics) at 37° C. for 1 hr. After a 5 min heat-inactivation at 98° C., primers complementary to the introduced universal tags (Table 6) were added to a final concentration of 0.5 uM each. These primers contained two terminal phosphorothioates to make them resistant to any residual Exonuclease-I activity. They also contained 5' grafting sequences necessary for hybridization to the Illumina GA IIx flow cell. Finally, they contained an index sequence between the grafting sequence and the universal tag sequence. This index sequence enables the PCR products from multiple different individuals to be simultaneously analyzed in the same flow cell compartment of the sequencer. The following cycling conditions were used for the subsequent 25 cycles of PCR: 98° C. for 10 s and 72° C. for 15 s. No intermediate purification steps were performed in an effort to reduce the losses of template molecules.

After the second round of amplification, wells were consolidated and purified using a Qiagen QIAquick PCR Purification Kit (cat. no. 28104) and eluted in 50 uL EB Buffer (Qiagen). Fragments of the expected size were purified after agarose (mtDNA libraries) or polyacrylamide (all other libraries) gel electrophoresis. For agarose gel purification, the eight 6-uL aliquots were loaded into wells of a 2% Size Select Gel (Invitrogen) and bands of the expected size were collected in EB Buffer as specified by the manufacturer. For polyacrylamide gel purification, ten 5-uL aliquots were loaded into wells of a 10% TBE Polyacrylamide Gel (Invitrogen). Gel slices containing the fragments of interest were excised, crushed, and eluted essentially as described (3).

Analysis of Phusion Polymerase Fidelity.

Amplification of a fragment of human genomic DNA within the BMX (RefSeq Accession NM_203281.2) gene was first performed using the PCR conditions described above. The template was diluted so that an average of one template molecule was present in every 10 wells of a 96-well PCR plate. Fifty uL PCR reactions were then performed in 1× Phusion HF buffer, 0.25 mM dNTPs, 0.5 uM each forward and reverse primers (Table 6), and 2 U of Phusion polymerase. The cycling conditions were one cycle of 98° C. for 30 s; and 19 cycles of 98° C. for 10 s, 61° C. for 120 s, and 72° C. for 10 s. The primers were removed by digestion with 60 U of Exonuclease-I at 37° C. for 1 hr followed by a 5 min heat-inactivation at 98° C. No purification of the PCR product was performed, either before or after Exonuclease-I digestion. The entire contents of each well were then used as templates for the exogenous UIDs strategy described above.

Sequencing.

Sequencing of all the libraries described above was performed using an Illumina GA IIx instrument as specified by the manufacturer. The total length of the reads used for each experiment varied from 36 to 73 bases. Base-calling and sequence alignment was performed with the Eland pipeline (Illumina). Only high quality reads meeting the following criteria were used for subsequent analysis: (i) the first 25 bases passed the standard Illumina chastity filter; (ii) every base in the read had a quality score ≥20; and (iii) ≤3 mismatches to expected sequences. For the exogenous UID libraries, we additionally required the UIDs to have a quality score ≥30. We noticed a relatively high frequency of errors at the ends of the reads in the endogenous UID libraries prepared with the standard Illumina protocol, presumably introduced during shearing or end-repair, so the first and last three bases of these tags were excluded from analysis.

Safe-SeqS Analysis.

High quality reads were grouped into UID-families based on their endogenous or exogenous UIDs. Only UID-families with two or more members were considered. Such UID-families included the vast majority (≥99%) of the sequencing reads. To ensure that the same data was used for both conventional and Safe-SeqS analysis, we also excluded UID-families containing only one member from conventional analysis. Furthermore, we only identified a base as "mutant" in conventional sequencing analysis if the same variant was identified in at least two members of at least one UID-family (i.e., two mutations) when comparing conventional analysis to that of Safe-SeqS with exogenous UIDs. For comparison with Safe-SeqS with endogenous UIDs, we required at least two members of each of two UID-families (i.e., four mutations) to identify a position as "mutant" in conventional analysis. With either endogenous or exogenous UIDs, a super-mutant was defined as a UID-family in which ≥95% of members shared the identical mutation. Thus, UID-families with <20 members had to be 100% identical at the mutant position, while a 5% combined replication and sequencing error rate was permitted in UID-families with more members. To determine polymerase fidelity using Safe-SeqS, and to compare the results with previous analyses of Phusion polymerase fidelity, it was necessary to realize that the previous analyses would only detect mutations present in both strands of the PCR products (4). This would be equivalent to analyzing PCR products generated with one less cycle with Safe-SeqS, and the appropriate correction was made in Table 2A. Unless otherwise specified, all values listed in the text and Tables represent means and standard deviations.

EXAMPLE 8

Error-Generating Processes

Apparent mutations, defined as any base call that varies from the expected base at a defined position, can result from a variety of processes:

1. Mutations present in the template DNA. For templates derived from normal human cells, these include mutations that were present in the zygote, occurred later during embryonic and adult development, or were present in a contaminant inadvertently introduced into the sample. These mutations are expected to be present in both strands of the relevant templates. If the mutation occurred only in the last cell-cycle of a cell whose DNA was used as template, the mutation would be present in only one strand of the template.
2. Chemically-modified bases present in the templates. It has been estimated that there are many thousands of oxidized bases present in every human cell (5). When such DNA is amplified by Phusion polymerase, an apparent mutation in one strand may result.
3. Errors introduced during the shearing process required to generate small fragments for sequencing. Acoustic shearing generates short-lived, high temperatures that can damage DNA.
4. Errors introduced during end-repair of the sheared fragments. The source of these errors can be polymerase infidelity or through incorporation of chemically-modified bases in the dNTPs used for polymerization.
5. Errors introduced by other enzymatic steps, particularly if the enzymes are impure and contaminated with nucleases, polymerases, or ligases.
6. Errors introduced during PCR amplification to prepare the libraries for capturing or for inverse PCR.
7. Errors during PCR after capturing or during inverse PCR amplification.
8. Errors introduced into the UID assignment cycles of Safe-SeqS (FIG. 3).
9. Errors introduced into the library amplification cycles of Safe-SeqS performed with exogenous UIDs. Note that if UID assignment primers from process #8 are not completely removed, they could potentially amplify DNA fragments containing errors introduced during these cycles, creating a new super-mutant.
10. Errors introduced into the first bridge-PCR cycle on the Illumina flow cell. If amplification is inefficient, an error introduced into the second bridge-PCR cycle could also result in a cluster containing a mutation in most of its component molecules.
11. Errors in base-calling.

EXAMPLE 9

Achieving Accuracy with Safe-SeqS

With conventional sequencing-by-synthesis approaches, all the error-producing processes described above are relevant, resulting in a relatively high number of false-positive mutation calls (Tables 1 and 2). Safe-SeqS minimizes the number of false-positive mutation calls in several ways. Safe-SeqS with exogenous UIDs results in the fewest false-positive mutation calls because it requires the fewest enzymatic steps. With exogenous UIDs, error-generating processes #3 to #7 are completely eliminated because these steps aren't performed. Safe-SeqS with exogenous UIDs also drastically reduces errors resulting from error-generating processes #10 and #11 because of the way the data is analyzed.

After Safe-SeqS with exogenous UIDs, the only false-positive errors remaining should be those introduced during the UID assignment PCR cycles (error-generating process #8) or residual UID-containing primers during the library amplification cycles (error-generating process #9). The errors from error-generating process #8 can theoretically be eliminated by requiring at least two super-mutants to identify a position as "mutant." This requirement is reasonable because every pre-existing mutation in a double stranded DNA template should give rise to two super-mutants, one from each strand. Furthermore, this requirement would eliminate error-generating process #2 (damaged bases in the original templates) because such bases, when copied, should give rise to only one super-mutant. Finally, errors generated during the library amplification cycles (process #9) will not be amplified by residual UID-containing primers if those primers are completely removed, such as performed here with excess Exonuclease-I.

With endogenous UIDs, the mistakes introduced by processes #10 and #11 are drastically reduced because of the way in which the data is analyzed (as with exogenous UIDs). Errors introduced in processes #2 to #7 can be minimized by requiring that a mutation be observed in at least two UID-families, for the reasons stated in the paragraph above. With this requirement, few false-positive mutations, in theory, should be identified.

In practice, the situation is complicated by the fact that the various amplifications are not perfect, so every strand of every original template molecule is not recovered as a UID-family. This efficiency can vary from sample to sample, depending in part on the concentration of inhibitors present in clinical samples. Moreover, with exogenous UIDs, a polymerase error during the library amplification step can create a new UID-family that wasn't represented in the UID assignment step. If this error occurred in a mutant template, an additional, artificial super-mutant would be created.

These factors can be managed by incorporating various additional criteria into the analyses. For example, one might require UID-families to contain more than two, five or ten members. Another requirement could be that the exogenous UIDs of super-mutants not be related to any other UID in the library by a one-base difference. This would eliminate artificial super-mutants generated during the library amplification steps (noted in above paragraph). We routinely instituted this requirement in our Safe-SeqS analyses, but it made little difference (<1%) in the number of super-mutants identified. Specificity for mutations can be further increased by requiring more than one super-mutant to identify a position as "mutant," as described above for endogenous UIDs. When requiring multiple super-mutants, the specificity can be even further increased by requiring that each strand of the original double stranded template contain the mutation or, when libraries are amplified using multiple wells, that rare mutations share an introduced sequence that identifies the well in which the mutations (i.e., one from each strand) were amplified. Such decisions involve the usual trade-off between specificity and sensitivity. In our experiments with exogenous UIDs (Table 2), we required only one super-mutant to identify a position as "mutant" and included all UID-families with more than one member. As endogenous UIDs was associated with more error-generating processes than with exogenous UIDs, we required two super-mutants to identify a position as mutant in the experiments reported in Table 1 and also included all UID-families with more than one member.

EXAMPLE 10

Mutation Prevalences in Normal Human Tissues

The experiments reported in Tables 1 and 2, in which >10,000 templates were assessed, show that mutations are present in the nuclear DNA of normal human cells at a frequency of $3.5 \times 10^{-6}$ to $9.0 \times 10^{-6}$ mutants/bp depending on the region analyzed. It is impossible to determine whether this low level represents genuine mutations present in the original templates or the sum of genuine mutations plus artifactual mutations from the error-generating processes described above. Mutation prevalences in human cells have not been widely investigated, in part because they are so infrequent. However, several clever techniques to identify rare mutants have been devised and can in principle be used for comparison. Unfortunately, estimates of human mutation prevalences vary widely, ranging from as many as $10^{-5}$ mutants/bp to as many as $10^{-8}$ mutants/bp (6-12). In several of these studies, the estimates are complicated by the lack of data on the nature of the actual mutations—they could in some cases be caused by losses of whole chromosomes, in others by missense mutations, and in others mainly by nonsense mutations or small insertions or deletions. Additionally, these studies used various sources of normal cells and examined different genes, making direct comparisons difficult. Estimates of the prevalences and rates of mitochondrial DNA mutations similarly vary (13-19). It will be of interest in future work to analyze the same DNA templates and genes with various technologies to determine the basis for these different estimates.

But let us assume that all of the mutations identified with Safe-SeqS represent genuine mutations present in the original DNA templates from normal cells. What does this tell us about the number of generations though which these cells have proceeded since the organism was conceived? There is a simple relationship between mutation rate and mutation prevalence: the mutation prevalence equals the product of the mutation rate and the number of generations that the cell has gone through since conception. The somatic mutation rate has been determined in previous studies to be ~$10^{-9}$ mutants/bp/generation, though this estimate also varies from study to study for reasons related to those mentioned above with respect to mutation prevalence. Combining this literature-derived estimate of mutation rate with our estimates of mutation prevalence suggests that the normal cells analyzed (lymphocytes, lymphoblastoid cell lines or colonic mucosae) had proceeded through 3,500 to 8,900 generations, representing cells dividing every 3 to 7 days for the individuals examined in this study (average age 65 years).

EXAMPLE 11

Computer Simulation of Polymerase-Introduced Errors

The timing of mutations introduced by polymerases greatly alters the final number of mutations observed (20). For example, two mutations would differ in prevalence by ~64-fold if introduced 6 cycles apart ($2^6$). Because polymerases introduce mutations in a stochastic manner, a simple Monte Carlo method was employed for the simulations. In these simulations, we used the manufacturer's estimate of the Phusion polymerase error rate with an appropriate adjustment for ability of Safe-SeqS to detect mutations in only one strand (4). Note that errors introduced in cycle 19, as well as in the two UID assignment cycles, would result in changes in only one strand of the duplex—i.e., result in one super-mutant rather than two. In each experiment, we assumed that there was a constant efficiency of amplification given by the total number of templates obtained at the end of the experiment (i.e., if the number of UID-families was N, then we assumed that the number of templates increased by a factor of $N/2^{19}$ in each cycle). One-thousand simulations were performed for each of seven experiments, and the results reported in Table 4.

REFERENCES

For Examples 8-11 Only

1. Herman D S, et al. (2009) Filter-based hybridization capture of subgenomes enables resequencing and copy-number detection. *Nat Methods* 6:507-510.
2. Vogeistein B & Kinzler K W (1999) Digital PCR. *Proc Natl Acad Sci USA* 96:9236-9241.
3. Chory J & Pollard J D, Jr. (2001) Separation of small DNA fragments by conventional gel electrophoresis. *Curr Protoc Mol Biol* Chapter 2:Unit2 7.
4. Barnes W M (1992) The fidelity of Taq polymerase catalyzing PCR is improved by an N-terminal deletion. *Gene* 112:29-35.
5. Collins A R (1999) Oxidative DNA damage, antioxidants, and cancer. *Bioessays* 21:238-246.
6. Morley A A, Cox S, & Holiday R (1982) Human lymphocytes resistant to 6-thioguanine increase with age. *Mech Ageing Dev* 19:21-26.
7. Trainor K J, et al. (1984) Mutation frequency in human lymphocytes increases with age. *Mech Ageing Dev* 27:83-86.
8. Grist S A, McCarron M, Kutlaca A, Turner D R, & Morley A A (1992) In vivo human somatic mutation: frequency and spectrum with age. *Mutat Res* 266:189-196.
9. Williams G T, Geraghty J M, Campbell F, Appleton M A, & Williams E D (1995) Normal colonic mucosa in hereditary non-polyposis colorectal cancer shows no generalised increase in somatic mutation. *Br J Cancer* 71:1077-1080.
10. Campbell F, Appleton M A, Shields C J, & Williams G T (1998) No difference in stem cell somatic mutation between the background mucosa of right- and left-sided sporadic colorectal carcinomas. *J Pathol* 186:31-35.
11. Araten D J, Nafa K, Pakdeesuwan K, & Luzzatto L (1999) Clonal populations of hematopoietic cells with paroxysmal nocturnal hemoglobinuria genotype and phenotype are present in normal individuals. *Proc Natl Acad Sci USA* 96:5209-5214.
12. Araten D J, et al. (2005) A quantitative measurement of the human somatic mutation rate. *Cancer Res* 65:8111-8117.
13. Monnat R J, Jr, & Loeb L A (1985) Nucleotide sequence preservation of human mitochondrial DNA. *Proc Natl Acad Sci USA* 82:2895-2899.
14. Bodenteich A, Mitchell L G, & Merril C R (1991) A lifetime of retinal light exposure does not appear to increase mitochondrial mutations. *Gene* 108:305-309.
15. Howell N, Kubacka I, & Mackey D A (1996) How rapidly does the human mitochondrial genome evolve? *Am J Hum Genet* 59:501-509.
16. Khrapko K, et al. (1997) Mitochondrial mutational spectra in human cells and tissues. *Proc Natl Acad Sci USA* 94:13798-13803.
17. Heyer E, et al. (2001) Phylogenetic and familial estimates of mitochondrial substitution rates: study of control region mutations in deep-rooting pedigrees. *Am J Hum Genet* 69:1113-1126.
18. Howell N, et al. (2003) The pedigree rate of sequence divergence in the human mitochondrial genome: there is a difference between phylogenetic and pedigree rates. *Am J Hum Genet* 72:659-670.
19. Taylor R W, et al. (2003) Mitochondrial DNA mutations in human colonic crypt stem cells. *J Clin Invest* 112:1351-1360.

20. Luria S E & Delbruck M (1943) Mutations of Bacteria from Virus Sensitivity to Virus Resistance. *Genetics* 28:491-511.

REFERENCES

For all Except Examples 8-11

The disclosure of each reference cited is expressly incorporated herein.

1. Luria S E & Delbruck M (1943) Mutations of Bacteria from Virus Sensitivity to Virus Resistance. *Genetics* 28:491-511.
2. Roach J C, et al. (2010) Analysis of genetic inheritance in a family quartet by whole-genome sequencing. *Science* 328:636-639.
3. Durbin R M, et al. (2010) A map of human genome variation from population-scale sequencing. *Nature* 467:1061-1073.
4. Shibata D (2011) Mutation and epigenetic molecular clocks in cancer. *Carcinogenesis* 32:123-128.
5. McMahon M A, et al. (2007) The HBV drug entecavir—effects on HIV-1 replication and resistance. *N Engl J Med* 356:2614-2621.
6. Eastman P S, et al. (1998) Maternal viral genotypic zidovudine resistance and infrequent failure of zidovudine therapy to prevent perinatal transmission of human immunodeficiency virus type 1 in pediatric AIDS Clinical Trials Group Protocol 076. *J Infect Dis* 177:557-564.
7. Chiu R W, et al. (2008) Noninvasive prenatal diagnosis of fetal chromosomal aneuploidy by massively parallel genomic sequencing of DNA in maternal plasma. *Proc Natl Acad Sci USA* 105:20458-20463.
8. Fan H C, Blumenfeld Y J, Chitkara U, Hudgins L, & Quake S R (2008) Noninvasive diagnosis of fetal aneuploidy by shotgun sequencing DNA from maternal blood. *Proc Natl Acad Sci USA* 105:16266-16271.
9. Hogue M O, et al. (2003) High-throughput molecular analysis of urine sediment for the detection of bladder cancer by high-density single-nucleotide polymorphism array. *Cancer Res* 63:5723-5726.
10. Thunnissen F B (2003) Sputum examination for early detection of lung cancer. *J Clin Pathol* 56:805-810.
11. Diehl F, et al. (2008) Analysis of mutations in DNA isolated from plasma and stool of colorectal cancer patients. *Gastroenterology* 135:489-498.
12. Barnes W M (1992) The fidelity of Taq polymerase catalyzing PCR is improved by an N-terminal deletion. *Gene* 112:29-35.
13. Araten D J, et al. (2005) A quantitative measurement of the human somatic mutation rate. *Cancer Res* 65:8111-8117.
14. Campbell F, Appleton M A, Shields C J, & Williams G T (1998) No difference in stem cell somatic mutation between the background mucosa of right- and left-sided sporadic colorectal carcinomas. *J Pathol* 186:31-35.
15. Tindall K R & Kunkel T A (1988) Fidelity of DNA synthesis by the Thermus aquaticus DNA polymerase, *Biochemistry* 27:6008-6013.
16. Kunkel T A (1985) The mutational specificity of DNA polymerase-beta during in vitro DNA synthesis. Production of frameshift, base substitution, and deletion mutations. *J Biol Chem* 260:5787-5796.
17. van Dongen J J & Wolvers-Tettero I L (1991) Analysis of immunoglobulin and T cell receptor genes. Part II: Possibilities and limitations in the diagnosis and management of lymphoproliferative diseases and related disorders. *Clin Chim Acta* 198:93-174.
18. Grist S A, McCarron M, Kutlaca A, Turner D R, & Morley A A (1992) In vivo human somatic mutation: frequency and spectrum with age. *Mutat Res* 266:189-196.
19. Liu Q & Sommer S S (2004) Detection of extremely rare alleles by bidirectional pyrophosphorolysis-activated polymerization allele-specific amplification (Bi-PAP-A): measurement of mutation load in mammalian tissues. *Biotechniques* 36:156-166.
20. Monnat R J, Jr. & Loeb L A (1985) Nucleotide sequence preservation of human mitochondrial DNA. *Proc Natl Acad Sci USA* 82:2895-2899.
21. Shi C. et al. (2004) LigAmp for sensitive detection of single-nucleotide differences, *Nat Methods* 1:141-147.
22. Keohavong P & Thilly W G (1989) Fidelity of DNA polymerases in DNA amplification. *Proc Natl Acad Sci USA* 86:9253-9257.
23. Sidransky D, et al. (1991) Identification of p53 gene mutations in bladder cancers and urine samples. *Science* 252:706-709.
24. Bielas J H & Loeb L A (2005) Quantification of random genomic mutations. *Nat Methods* 2:285-290.
25. Vogelstein B & Kinzler K W (1999) Digital PCR. *Proc Natl Acad Sci USA* 96:9236-9241.
26. Mitra R D, et al. (2003) Digital genotyping and haplotyping with polymerase colonies. *Proc Natl Acad Sci USA* 100:5926-5931.
27. Chetverina H V, Samatov T R, Ugarov V I, & Chetverin A B (2002) Molecular colony diagnostics: detection and quantitation of viral nucleic acids by in-gel PCR. *Biotechniques* 33:150-152, 154, 156.
28. Zimmermann B G, et al. (2008) Digital PCR: a powerful new tool for noninvasive prenatal diagnosis? *Prenat Diagn* 28:1087-1093.
29. Dressman D, Yan H, Traverso G, Kinzler K W, & Vogelstein B (2003) Transforming single DNA molecules into fluorescent magnetic particles for detection and enumeration of genetic variations. *Proc Natl Acad Sci USA* 100:8817-8822.
30. Ottesen E A, Hong J W, Quake S R, & Leadbetter J R (2006) Microfluidic digital PCR enables multigene analysis of individual environmental bacteria. *Science* 314:1464-1467.
31. Quail M A, et al. (2008) A large genome center's improvements to the Illumina sequencing system. *Nat Methods* 5:1005-1010.
32. Nazarian R, et al. (2010) Melanomas acquire resistance to B-RAF(V600E) inhibition by RTK or N-RAS upregulation. *Nature* 468:973-977.
33. He Y, et al. (2010) Heteroplasmic mitochondrial DNA mutations in normal and tumour cells. *Nature* 464:610-614.
34. Gore A, et al. (2011) Somatic coding mutations in human induced pluripotent stem cells. *Nature* 471:63-67.
35. Dohm J C, Lottaz C, Borodina T, & Himmelbauer H (2008) Substantial biases in ultra-short read data sets from high-throughput sequencing. *Nucleic Acids Res* 36:e105.
36. Erlich Y, Mitra P P, delaBastide M, McCombie W R, & Hannon G J (2008) Alta-Cyclic: a self-optimizing base caller for next-generation sequencing. *Nat Methods* 5:679-682.
37. Rougemont J, et al. (2008) Probabilistic base calling of Solexa sequencing data. *BMC Bioinformatics* 9:431.

38. Druley T E, et al. (2009) Quantification of rare allelic variants from pooled genomic DNA, *Nat Methods* 6:263-265.
39. Vallania F L, et al. (2010) High-throughput discovery of rare insertions and deletions in large cohorts. *Genome Res* 20:1711-1718.
40. McCloskey M L, Stoger R, Hansen R S, & Laird C D (2007) Encoding PCR products with batch-stamps and barcodes. *Biochem Genet* 45:761-767.
41. Parameswaran P, et al. (2007) A pyrosequencing-tailored nucleotide barcode design unveils opportunities for large-scale sample multiplexing. *Nucleic Acids Res* 35:e130.
42. Craig D W, et al. (2008) Identification of genetic variants using bar-coded multiplexed sequencing. *Nat Methods* 5:887-893.
43. Miner B E, Stoger R J, Burden A F, Laird C D, & Hansen R S (2004) Molecular barcodes detect redundancy and contamination in hairpin-bisulfite PCR. *Nucleic Acids Res* 32:e135.
44. Herman D S, et al. (2009) Filter-based hybridization capture of subgenomes enables resequencing and copy-number detection. *Nat Methods* 6:507-510.
45. Jones P A & Baylin S B (2007) The epigenomics of cancer. *Cell* 128:683-692.
46. de Boer J G & Ripley L S (1988) An in vitro assay for frameshift mutations: hotspots for deletions of 1 bp by Klenow-fragment polymerase share a consensus DNA sequence. *Genetics* 118:181-191.
47. Eckert K A & Kunkel T A (1990) High fidelity DNA synthesis by the Thermus aquaticus DNA polymerase. *Nucleic Acids Res* 18:3739-3744.
48. Kosuri S, et al. (2010) Scalable gene synthesis by selective amplification of DNA pools from high-fidelity microchips. *Nat Biotechnol* 28:1295-1299.
49. Matzas M, et al. (2010) High-fidelity gene synthesis by retrieval of sequence-verified DNA identified using high-throughput pyrosequencing. *Nat Biotechnol* 28:1291-1294.
50. Li J, et al. (2008) Replacing PCR with COLD-PCR enriches variant DNA sequences and redefines the sensitivity of genetic testing. *Nat Med* 14:579-584.
51. Eid J, et al. (2009) Real-time DNA sequencing from single polymerase molecules. *Science* 323:133-138.

The invention claimed is:

1. A method to analyze nucleic acid sequences, comprising:
    attaching a unique identifier nucleic acid sequence (UID) from a pool of UIDs to a first end of each strand of a plurality of analyte nucleic acid fragments to form a plurality of uniquely identified analyte nucleic acid fragments wherein the pool of UIDs is in excess of the plurality of analyte nucleic acid fragments;
    redundantly determining nucleotide sequence of a uniquely identified analyte nucleic acid fragment, wherein determined nucleotide sequences which share a UID form a family of members;
    comparing determined nucleotide sequences between members of a family; and
    identifying a nucleotide sequence as accurately representing an analyte nucleic acid fragment when at least 5% of members of the family contain the sequence and wherein the family contains at least 2 members.

2. The method of claim 1 wherein prior to the step of redundantly determining, the uniquely identified analyte nucleic acid fragments are amplified.

3. The method of claim 1 wherein the nucleotide sequence is identified when at least 25% of members of the family contain the sequence.

4. The method of claim 1 wherein the nucleotide sequence is identified when at 50% of members of the family contain the sequence.

5. The method of claim 1 wherein the nucleotide sequence is identified when at least 70% of members of the family contain the sequence.

6. The method of claim 1 wherein the nucleotide sequence is identified when at least 90% of members of the family contain the sequence.

7. The method of claim 1 wherein the nucleotide sequence is identified when 100% of members of the family contain the sequence.

8. The method of claim 1 wherein the step of attaching is performed by polymerase chain reaction.

9. The method of claim 1 wherein a first universal priming site is attached to a second end of each of a plurality of analyte nucleic acid fragments.

10. The method of claim 8 wherein at least two cycles of polymerase chain reaction are performed such that a family is formed of uniquely identified analyte nucleic acid fragments that have a UID on the first end and a first universal priming site on a second end.

11. The method of claim 1 wherein the UID is covalently linked to a second universal priming site.

12. The method of claim 9 wherein the UID is covalently linked to a second universal priming site.

13. The method of claim 12 wherein prior to the step of redundantly determining, the uniquely identified analyte nucleic acid fragments are amplified using a pair of primers which are complementary to the first and the second universal priming sites, respectively.

14. The method of claim 11 wherein the UID is attached to the 5' end of an analyte nucleic acid fragment and the second universal priming site is 5' to the UID.

15. The method of claim 11 wherein the UID is attached to the 3' end of an analyte nucleic acid fragment and the second universal priming site is 3' to the UID.

16. The method of claim 1 wherein the analyte nucleic acid fragments are formed by applying a shear force to analyte nucleic acid.

17. The method of claim 8 wherein prior to the step of redundantly determining, the uniquely identified analyte nucleic acid fragments are subjected to amplification, and wherein prior to said amplification, a single strand-specific exonuclease is used to digest excess primers used to attach the UID the analyte nucleic acid fragments.

18. The method of claim 17 wherein prior to the step of redundantly determining, the uniquely identified analyte nucleic acid fragments are subject to amplification, and wherein prior to said amplification, the single strand-specific exonuclease is inactivated, inhibited, or removed.

19. The method of claim 18 wherein the single strand-specific exonuclease is inactivated by heat treatment.

20. The method of claim 17 wherein primers used in said amplification comprise one or more chemical modifications rendering them resistant to exonucleases.

21. The method of claim 17 wherein primers used in said amplification comprise one or more phosphorothioate linkages.

22. The method of claim 2 wherein prior to the amplification, the analyte nucleic acid is treated with bisulfite to convert unmethylated cytosine bases to uracil.

23. The method of claim 1 further comprising the step of comparing number of families representing a first analyte DNA fragment to number of families representing a second analyte DNA fragment to determine a relative concentration of a first analyte DNA fragment to a second analyte DNA fragment in the plurality of analyte nucleic acid fragments.

24. The method of claim 8 wherein the UIDs are in excess of the analyte nucleic acid fragments during the polymerase chain reaction.

25. The method of claim 1 wherein the UIDs are from 2 to 4000 bases inclusive.

26. The method of claim 1 wherein a nucleotide sequence is identified as accurately representing an analyte DNA fragment when the sequence is present in only one of two strands of the analyte DNA fragment.

27. The method of claim 1 wherein a nucleotide sequence is identified as accurately representing an analyte DNA fragment when the sequence is present in both of two strands of the analyte DNA fragment.

28. The method of claim 1 further comprising the step of:
    identifying a mutation when the nucleotide sequence that accurately represents the analyte nucleic acid fragment is different from a reference sequence.

29. The method of claim 1 further comprising:
    identifying a determined nucleotide sequence as an error introduced during processing when less than 5% of members of the family contain the sequence.

30. The method of claim 1 further comprising:
    identifying a determined nucleotide sequence as an error introduced during processing when less than 1% of members of the family contain the sequence.

31. The method of claim 28 wherein a mutation is identified when the nucleotide sequence that accurately represents the analyte nucleic acid fragment is found in at least two families.

32. The method of claim 28 wherein the mutation is a single base substitution an insertion, or a deletion.

33. The method of claim 1 wherein a nucleotide sequence is identified as accurately representing an analyte nucleic acid fragment when at least 5% of members of the family contain the sequence and wherein the family contains at least 20 members.

34. A method to analyze nucleic acid sequences, comprising:
    attaching a unique identifier nucleic acid sequence (UID) of 2-4000 bases from a pool of UIDs to a first end of each strand of a plurality of analyte nucleic acid fragments using at least two cycles of polymerase chain reaction to form uniquely identified analyte nucleic acid fragments, wherein the pool of UIDs is in excess of the plurality of analyte nucleic acid fragments;

redundantly determining nucleotide sequence of a uniquely identified analyte nucleic acid fragment, wherein determined nucleotide sequences which share a UID form a family of members;

comparing determined nucleotide sequences between members of a family;

identifying a nucleotide sequence as accurately representing an analyte nucleic acid fragment when at least 50% of members of the family contain the sequence and wherein the family contains at least 2 members; and comparing the nucleotide sequence identified as accurately representing an analyte nucleic acid fragment to a reference sequence and identifying a single base substitution, insertion, or deletion in the nucleotide sequence relative to the reference sequence.

* * * * *

UNITED STATES PATENT AND TRADEMARK OFFICE
CERTIFICATE OF CORRECTION

PATENT NO. : 9,476,095 B2
APPLICATION NO. : 14/111715
DATED : October 25, 2016
INVENTOR(S) : Bert Vogelstein et al.

Page 1 of 1

It is certified that error appears in the above-identified patent and that said Letters Patent is hereby corrected as shown below:

In Column 1, Lines 3-6, replace the first paragraph as follows:
STATEMENT OF GOVERNMENTAL INTEREST
This invention was made with government support under grant number CA062924, CA057345, CA043460, CN043309, awarded by the National Institutes of Health. The government has certain rights in the invention.

Signed and Sealed this
Twentieth Day of February, 2018

Andrei Iancu
*Director of the United States Patent and Trademark Office*

UNITED STATES PATENT AND TRADEMARK OFFICE
CERTIFICATE OF CORRECTION

| | |
|---|---|
| PATENT NO. | : 9,476,095 B2 |
| APPLICATION NO. | : 14/111715 |
| DATED | : October 25, 2016 |
| INVENTOR(S) | : Bert Vogelstein et al. |

Page 1 of 1

It is certified that error appears in the above-identified patent and that said Letters Patent is hereby corrected as shown below:

In the Specification

Column 1, Lines 3-6, replace:
"This invention was made using support from The National Institutes of Health, grants CA62924, CA43460, and CA57345. Certain rights to the invention are retained by the U.S. government under the terms of the grant."

With:
--STATEMENT OF FEDERALLY SPONSORED RESEARCH
This invention was made with government support under Grant nos. CA62924, CA43460, and CA57345, awarded by the National Institutes of Health. The government has certain rights in the invention.--

This certificate supersedes the Certificate of Correction issued February 20, 2018.

Signed and Sealed this
Twenty-sixth Day of May, 2020

Andrei Iancu
*Director of the United States Patent and Trademark Office*

SEQUENCE LISTING

```
<160> NUMBER OF SEQ ID NOS: 81

<210> SEQ ID NO 1
<211> LENGTH: 32
<212> TYPE: DNA
<213> ORGANISM: Artificial Sequence
<220> FEATURE:
<223> OTHER INFORMATION: Primers and adapters

<400> SEQUENCE: 1
gatcggaaga gcggttcagc aggaatgccg ag                                   32

<210> SEQ ID NO 2
<211> LENGTH: 33
<212> TYPE: DNA
<213> ORGANISM: Artificial Sequence
<220> FEATURE:
<223> OTHER INFORMATION: Primers and adapters

<400> SEQUENCE: 2
acactctttc cctacacgac gctcttccga tct                                  33

<210> SEQ ID NO 3
<211> LENGTH: 62
<212> TYPE: DNA
<213> ORGANISM: Artificial Sequence
<220> FEATURE:
<223> OTHER INFORMATION: Primers and adapters

<400> SEQUENCE: 3
aatgatacgg cgaccaccga gatctacaca cactctttcc ctacacgacg ctcttccgat     60
ct                                                                    62

<210> SEQ ID NO 4
<211> LENGTH: 57
<212> TYPE: DNA
<213> ORGANISM: Artificial Sequence
<220> FEATURE:
<223> OTHER INFORMATION: Primers and adapters

<400> SEQUENCE: 4
caagcagaag acggcatacg agatctcggc attcctgctg aaccgctctt ccgatct        57
```

```
<210> SEQ ID NO 5
<211> LENGTH: 62
<212> TYPE: DNA
<213> ORGANISM: Artificial Sequence
<220> FEATURE:
<223> OTHER INFORMATION: Primers and adapters

<400> SEQUENCE: 5
aatgatacgg cgaccaccga gatctacaca cactctttcc ctacacgacg ctcttccgat      60
ct                                                                    62

<210> SEQ ID NO 6
<211> LENGTH: 57
<212> TYPE: DNA
<213> ORGANISM: Artificial Sequence
<220> FEATURE:
<223> OTHER INFORMATION: Primers and adapters

<400> SEQUENCE: 6
caagcagaag acggcatacg agatctcggc attcctgctg aaccgctctt ccgatct         57

<210> SEQ ID NO 7
<211> LENGTH: 33
<212> TYPE: DNA
<213> ORGANISM: Artificial Sequence
<220> FEATURE:
<223> OTHER INFORMATION: Primers and adapters

<400> SEQUENCE: 7
acactctttc cctacacgac gctcttccga tct                                  33

<210> SEQ ID NO 8
<211> LENGTH: 33
<212> TYPE: DNA
<213> ORGANISM: Artificial Sequence
<220> FEATURE:
<223> OTHER INFORMATION: Primers and adapters

<400> SEQUENCE: 8
ctcggcattc ctgctgaacc gctcttccga tct                                  33

<210> SEQ ID NO 9
<211> LENGTH: 32
<212> TYPE: DNA
<213> ORGANISM: Artificial Sequence
<220> FEATURE:
<223> OTHER INFORMATION: Primers and adapters

<400> SEQUENCE: 9
gatcggaaga gcggttcagc aggaatgccg ag                                   32

<210> SEQ ID NO 10
<211> LENGTH: 33
<212> TYPE: DNA
<213> ORGANISM: Artificial Sequence
<220> FEATURE:
<223> OTHER INFORMATION: Primers and adapters

<400> SEQUENCE: 10
acactctttc cctacacgac gctcttccga tct                                  33

<210> SEQ ID NO 11
<211> LENGTH: 39
<212> TYPE: DNA
```

```
<213> ORGANISM: Artificial Sequence
<220> FEATURE:
<223> OTHER INFORMATION: Primers and adapters

<400> SEQUENCE: 11
cgtgatacac tctttcccta cacgacgctc ttccgatct                     39

<210> SEQ ID NO 12
<211> LENGTH: 39
<212> TYPE: DNA
<213> ORGANISM: Artificial Sequence
<220> FEATURE:
<223> OTHER INFORMATION: Primers and adapters

<400> SEQUENCE: 12
acatcgacac tctttcccta cacgacgctc ttccgatct                     39

<210> SEQ ID NO 13
<211> LENGTH: 39
<212> TYPE: DNA
<213> ORGANISM: Artificial Sequence
<220> FEATURE:
<223> OTHER INFORMATION: Primers and adapters

<400> SEQUENCE: 13
gcctaaacac tctttcccta cacgacgctc ttccgatct                     39

<210> SEQ ID NO 14
<211> LENGTH: 39
<212> TYPE: DNA
<213> ORGANISM: Artificial Sequence
<220> FEATURE:
<223> OTHER INFORMATION: Primers and adapters

<400> SEQUENCE: 14
tggtcaacac tctttcccta cacgacgctc ttccgatct                     39

<210> SEQ ID NO 15
<211> LENGTH: 39
<212> TYPE: DNA
<213> ORGANISM: Artificial Sequence
<220> FEATURE:
<223> OTHER INFORMATION: Primers and adapters

<400> SEQUENCE: 15
cactgtacac tctttcccta cacgacgctc ttccgatct                     39

<210> SEQ ID NO 16
<211> LENGTH: 39
<212> TYPE: DNA
<213> ORGANISM: Artificial Sequence
<220> FEATURE:
<223> OTHER INFORMATION: Primers and adapters

<400> SEQUENCE: 16
attggcacac tctttcccta cacgacgctc ttccgatct                     39

<210> SEQ ID NO 17
<211> LENGTH: 39
<212> TYPE: DNA
<213> ORGANISM: Artificial Sequence
<220> FEATURE:
<223> OTHER INFORMATION: Primers and adapters

<400> SEQUENCE: 17
gatctgacac tctttcccta cacgacgctc ttccgatct                     39
```

<210> SEQ ID NO 18
<211> LENGTH: 39
<212> TYPE: DNA
<213> ORGANISM: Artificial Sequence
<220> FEATURE:
<223> OTHER INFORMATION: Primers and adapters

<400> SEQUENCE: 18
tcaagtacac tctttcccta cacgacgctc ttccgatct                   39

<210> SEQ ID NO 19
<211> LENGTH: 39
<212> TYPE: DNA
<213> ORGANISM: Artificial Sequence
<220> FEATURE:
<223> OTHER INFORMATION: Primers and adapters

<400> SEQUENCE: 19
ctgatcacac tctttcccta cacgacgctc ttccgatct                   39

<210> SEQ ID NO 20
<211> LENGTH: 39
<212> TYPE: DNA
<213> ORGANISM: Artificial Sequence
<220> FEATURE:
<223> OTHER INFORMATION: Primers and adapters

<400> SEQUENCE: 20
aagctaacac tctttcccta cacgacgctc ttccgatct                   39

<210> SEQ ID NO 21
<211> LENGTH: 39
<212> TYPE: DNA
<213> ORGANISM: Artificial Sequence
<220> FEATURE:
<223> OTHER INFORMATION: Primers and adapters

<400> SEQUENCE: 21
gtagccacac tctttcccta cacgacgctc ttccgatct                   39

<210> SEQ ID NO 22
<211> LENGTH: 39
<212> TYPE: DNA
<213> ORGANISM: Artificial Sequence
<220> FEATURE:
<223> OTHER INFORMATION: Primers and adapters

<400> SEQUENCE: 22
tacaagacac tctttcccta cacgacgctc ttccgatct                   39

<210> SEQ ID NO 23
<211> LENGTH: 33
<212> TYPE: DNA
<213> ORGANISM: Artificial Sequence
<220> FEATURE:
<223> OTHER INFORMATION: Primers and adapters

<400> SEQUENCE: 23
ctcggcattc ctgctgaacc gctcttccga tct                         33

<210> SEQ ID NO 24
<211> LENGTH: 56
<212> TYPE: DNA
<213> ORGANISM: Artificial Sequence
<220> FEATURE:

<223> OTHER INFORMATION: Primers and adapters

<400> SEQUENCE: 24
aatgatacgg cgaccaccga gatctacacc agcaggcctt ataataaaaa taatga         56

<210> SEQ ID NO 25
<211> LENGTH: 51
<212> TYPE: DNA
<213> ORGANISM: Artificial Sequence
<220> FEATURE:
<223> OTHER INFORMATION: Primers and adapters

<400> SEQUENCE: 25
caagcagaag acggcatacg agattgactg aatataaact tgtggtagtt g              51

<210> SEQ ID NO 26
<211> LENGTH: 33
<212> TYPE: DNA
<213> ORGANISM: Artificial Sequence
<220> FEATURE:
<223> OTHER INFORMATION: Primers and adapters

<400> SEQUENCE: 26
acactctttc cctacacgac gctcttccga tct                                  33

<210> SEQ ID NO 27
<211> LENGTH: 33
<212> TYPE: DNA
<213> ORGANISM: Artificial Sequence
<220> FEATURE:
<223> OTHER INFORMATION: Primers and adapters

<400> SEQUENCE: 27
ctcggcattc ctgctgaacc gctcttccga tct                                  33

<210> SEQ ID NO 28
<211> LENGTH: 29
<212> TYPE: DNA
<213> ORGANISM: Artificial Sequence
<220> FEATURE:
<223> OTHER INFORMATION: Primers and adapters

<400> SEQUENCE: 28
cggaagagcg tcgtgtaggg aaagagtgt                                       29

<210> SEQ ID NO 29
<211> LENGTH: 29
<212> TYPE: DNA
<213> ORGANISM: Artificial Sequence
<220> FEATURE:
<223> OTHER INFORMATION: Primers and adapters

<400> SEQUENCE: 29
cggaagagcg gttcagcagg aatgccgag                                       29

<210> SEQ ID NO 30
<211> LENGTH: 23
<212> TYPE: DNA
<213> ORGANISM: Artificial Sequence
<220> FEATURE:
<223> OTHER INFORMATION: Primers and adapters

<400> SEQUENCE: 30
ggttacaggc tcatgatgta acc                                             23

```
<210> SEQ ID NO 31
<211> LENGTH: 21
<212> TYPE: DNA
<213> ORGANISM: Artificial Sequence
<220> FEATURE:
<223> OTHER INFORMATION: Primers and adapters

<400> SEQUENCE: 31
gataccagct tggtaatggc a                                              21

<210> SEQ ID NO 32
<211> LENGTH: 56
<212> TYPE: DNA
<213> ORGANISM: Artificial Sequence
<220> FEATURE:
<223> OTHER INFORMATION: Primers and adapters
<221> NAME/KEY: misc_feature
<222> LOCATION: (1)...(56)
<223> OTHER INFORMATION: n = A,T,C or G

<400> SEQUENCE: 32
cgacgtaaaa cgacggccag tnnnnnnnnn nnnggttaca ggctcatgat gtaacc        56

<210> SEQ ID NO 33
<211> LENGTH: 46
<212> TYPE: DNA
<213> ORGANISM: Artificial Sequence
<220> FEATURE:
<223> OTHER INFORMATION: Primers and adapters

<400> SEQUENCE: 33
cacacaggaa acagctatga ccatggatac cagcttggta atggca                   46

<210> SEQ ID NO 34
<211> LENGTH: 56
<212> TYPE: DNA
<213> ORGANISM: Artificial Sequence
<220> FEATURE:
<223> OTHER INFORMATION: Primers and adapters

<400> SEQUENCE: 34
aatgatacgg cgaccaccga gatctacacc gtgatcgacg taaaacgacg gccagt        56

<210> SEQ ID NO 35
<211> LENGTH: 56
<212> TYPE: DNA
<213> ORGANISM: Artificial Sequence
<220> FEATURE:
<223> OTHER INFORMATION: Primers and adapters

<400> SEQUENCE: 35
aatgatacgg cgaccaccga gatctacaca catcgcgacg taaaacgacg gccagt        56

<210> SEQ ID NO 36
<211> LENGTH: 56
<212> TYPE: DNA
<213> ORGANISM: Artificial Sequence
<220> FEATURE:
<223> OTHER INFORMATION: Primers and adapters

<400> SEQUENCE: 36
aatgatacgg cgaccaccga gatctacacg cctaacgacg taaaacgacg gccagt        56

<210> SEQ ID NO 37
<211> LENGTH: 56
<212> TYPE: DNA
<213> ORGANISM: Artificial Sequence
```

```
<220> FEATURE:
<223> OTHER INFORMATION: Primers and adapters

<400> SEQUENCE: 37
aatgatacgg cgaccaccga gatctacact ggtcacgacg taaaacgacg gccagt      56

<210> SEQ ID NO 38
<211> LENGTH: 56
<212> TYPE: DNA
<213> ORGANISM: Artificial Sequence
<220> FEATURE:
<223> OTHER INFORMATION: Primers and adapters

<400> SEQUENCE: 38
aatgatacgg cgaccaccga gatctacacc actgtcgacg taaaacgacg gccagt      56

<210> SEQ ID NO 39
<211> LENGTH: 56
<212> TYPE: DNA
<213> ORGANISM: Artificial Sequence
<220> FEATURE:
<223> OTHER INFORMATION: Primers and adapters

<400> SEQUENCE: 39
aatgatacgg cgaccaccga gatctacaca ttggccgacg taaaacgacg gccagt      56

<210> SEQ ID NO 40
<211> LENGTH: 56
<212> TYPE: DNA
<213> ORGANISM: Artificial Sequence
<220> FEATURE:
<223> OTHER INFORMATION: Primers and adapters

<400> SEQUENCE: 40
aatgatacgg cgaccaccga gatctacacg atctgcgacg taaaacgacg gccagt      56

<210> SEQ ID NO 41
<211> LENGTH: 56
<212> TYPE: DNA
<213> ORGANISM: Artificial Sequence
<220> FEATURE:
<223> OTHER INFORMATION: Primers and adapters

<400> SEQUENCE: 41
aatgatacgg cgaccaccga gatctacact caagtcgacg taaaacgacg gccagt      56

<210> SEQ ID NO 42
<211> LENGTH: 56
<212> TYPE: DNA
<213> ORGANISM: Artificial Sequence
<220> FEATURE:
<223> OTHER INFORMATION: Primers and adapters

<400> SEQUENCE: 42
aatgatacgg cgaccaccga gatctacacc tgatccgacg taaaacgacg gccagt      56

<210> SEQ ID NO 43
<211> LENGTH: 56
<212> TYPE: DNA
<213> ORGANISM: Artificial Sequence
<220> FEATURE:
<223> OTHER INFORMATION: Primers and adapters

<400> SEQUENCE: 43
aatgatacgg cgaccaccga gatctacaca agctacgacg taaaacgacg gccagt      56
```

```
<210> SEQ ID NO 44
<211> LENGTH: 49
<212> TYPE: DNA
<213> ORGANISM: Artificial Sequence
<220> FEATURE:
<223> OTHER INFORMATION: Primers and adapters

<400> SEQUENCE: 44
caagcagaag acggcatacg agatcacaca ggaaacagct atgaccatg          49

<210> SEQ ID NO 45
<211> LENGTH: 21
<212> TYPE: DNA
<213> ORGANISM: Artificial Sequence
<220> FEATURE:
<223> OTHER INFORMATION: Primers and adapters

<400> SEQUENCE: 45
cgacgtaaaa cgacggccag t                                        21

<210> SEQ ID NO 46
<211> LENGTH: 21
<212> TYPE: DNA
<213> ORGANISM: Artificial Sequence
<220> FEATURE:
<223> OTHER INFORMATION: Primers and adapters

<400> SEQUENCE: 46
actggccgtc gttttacgtc g                                        21

<210> SEQ ID NO 47
<211> LENGTH: 58
<212> TYPE: DNA
<213> ORGANISM: Artificial Sequence
<220> FEATURE:
<223> OTHER INFORMATION: Primers and adapters
<221> NAME/KEY: misc_feature
<222> LOCATION: (1)...(58)
<223> OTHER INFORMATION: n = A,T,C or G

<400> SEQUENCE: 47
cgacgtaaaa cgacggccag tnnnnnnnnn nnnnngcagc aacagtctta cctggact  58

<210> SEQ ID NO 48
<211> LENGTH: 48
<212> TYPE: DNA
<213> ORGANISM: Artificial Sequence
<220> FEATURE:
<223> OTHER INFORMATION: Primers and adapters

<400> SEQUENCE: 48
cacacaggaa acagctatga ccatgtccac atcctcttcc tcaggatt           48

<210> SEQ ID NO 49
<211> LENGTH: 50
<212> TYPE: DNA
<213> ORGANISM: Artificial Sequence
<220> FEATURE:
<223> OTHER INFORMATION: Primers and adapters

<400> SEQUENCE: 49
aatgatacgg cgaccaccga gatctacacc gacgtaaaac gacggccagt         50

<210> SEQ ID NO 50
<211> LENGTH: 55
<212> TYPE: DNA
```

<213> ORGANISM: Artificial Sequence
<220> FEATURE:
<223> OTHER INFORMATION: Primers and adapters

<400> SEQUENCE: 50
caagcagaag acggcatacg agatatcacg cacacaggaa acagctatga ccatg     55

<210> SEQ ID NO 51
<211> LENGTH: 55
<212> TYPE: DNA
<213> ORGANISM: Artificial Sequence
<220> FEATURE:
<223> OTHER INFORMATION: Primers and adapters

<400> SEQUENCE: 51
caagcagaag acggcatacg agatcgatgt cacacaggaa acagctatga ccatg     55

<210> SEQ ID NO 52
<211> LENGTH: 55
<212> TYPE: DNA
<213> ORGANISM: Artificial Sequence
<220> FEATURE:
<223> OTHER INFORMATION: Primers and adapters

<400> SEQUENCE: 52
caagcagaag acggcatacg agattgacca cacacaggaa acagctatga ccatg     55

<210> SEQ ID NO 53
<211> LENGTH: 55
<212> TYPE: DNA
<213> ORGANISM: Artificial Sequence
<220> FEATURE:
<223> OTHER INFORMATION: Primers and adapters

<400> SEQUENCE: 53
caagcagaag acggcatacg agatgccaat cacacaggaa acagctatga ccatg     55

<210> SEQ ID NO 54
<211> LENGTH: 55
<212> TYPE: DNA
<213> ORGANISM: Artificial Sequence
<220> FEATURE:
<223> OTHER INFORMATION: Primers and adapters

<400> SEQUENCE: 54
caagcagaag acggcatacg agatcagatc cacacaggaa acagctatga ccatg     55

<210> SEQ ID NO 55
<211> LENGTH: 55
<212> TYPE: DNA
<213> ORGANISM: Artificial Sequence
<220> FEATURE:
<223> OTHER INFORMATION: Primers and adapters

<400> SEQUENCE: 55
caagcagaag acggcatacg agatacttga cacacaggaa acagctatga ccatg     55

<210> SEQ ID NO 56
<211> LENGTH: 55
<212> TYPE: DNA
<213> ORGANISM: Artificial Sequence
<220> FEATURE:
<223> OTHER INFORMATION: Primers and adapters

<400> SEQUENCE: 56
caagcagaag acggcatacg agatgatcag cacacaggaa acagctatga ccatg     55

<210> SEQ ID NO 57
<211> LENGTH: 55
<212> TYPE: DNA
<213> ORGANISM: Artificial Sequence
<220> FEATURE:
<223> OTHER INFORMATION: Primers and adapters

<400> SEQUENCE: 57
caagcagaag acggcatacg agattagctt cacacaggaa acagctatga ccatg     55

<210> SEQ ID NO 58
<211> LENGTH: 55
<212> TYPE: DNA
<213> ORGANISM: Artificial Sequence
<220> FEATURE:
<223> OTHER INFORMATION: Primers and adapters

<400> SEQUENCE: 58
caagcagaag acggcatacg agatggctac cacacaggaa acagctatga ccatg     55

<210> SEQ ID NO 59
<211> LENGTH: 55
<212> TYPE: DNA
<213> ORGANISM: Artificial Sequence
<220> FEATURE:
<223> OTHER INFORMATION: Primers and adapters

<400> SEQUENCE: 59
caagcagaag acggcatacg agatcttgta cacacaggaa acagctatga ccatg     55

<210> SEQ ID NO 60
<211> LENGTH: 21
<212> TYPE: DNA
<213> ORGANISM: Artificial Sequence
<220> FEATURE:
<223> OTHER INFORMATION: Primers and adapters

<400> SEQUENCE: 60
cgacgtaaaa cgacggccag t                                          21

<210> SEQ ID NO 61
<211> LENGTH: 25
<212> TYPE: DNA
<213> ORGANISM: Artificial Sequence
<220> FEATURE:
<223> OTHER INFORMATION: Primers and adapters

<400> SEQUENCE: 61
catggtcata gctgtttcct gtgtg                                      25

<210> SEQ ID NO 62
<211> LENGTH: 57
<212> TYPE: DNA
<213> ORGANISM: Artificial Sequence
<220> FEATURE:
<223> OTHER INFORMATION: Primers and adapters
<221> NAME/KEY: misc_feature
<222> LOCATION: (1)...(57)
<223> OTHER INFORMATION: n = A,T,C or G

<400> SEQUENCE: 62
cgacgtaaaa cgacggccag tnnnnnnnnn nnnnnttacc gagaaagctc acaagaa   57

<210> SEQ ID NO 63
<211> LENGTH: 45

```
<212> TYPE: DNA
<213> ORGANISM: Artificial Sequence
<220> FEATURE:
<223> OTHER INFORMATION: Primers and adapters

<400> SEQUENCE: 63
cacacaggaa acagctatga ccatgatgct aaggcgagga tgaaa            45

<210> SEQ ID NO 64
<211> LENGTH: 56
<212> TYPE: DNA
<213> ORGANISM: Artificial Sequence
<220> FEATURE:
<223> OTHER INFORMATION: Primers and adapters

<400> SEQUENCE: 64
aatgatacgg cgaccaccga gatctacaca catcgcgacg taaaacgacg gccagt   56

<210> SEQ ID NO 65
<211> LENGTH: 56
<212> TYPE: DNA
<213> ORGANISM: Artificial Sequence
<220> FEATURE:
<223> OTHER INFORMATION: Primers and adapters

<400> SEQUENCE: 65
aatgatacgg cgaccaccga gatctacacg cctaacgacg taaaacgacg gccagt   56

<210> SEQ ID NO 66
<211> LENGTH: 56
<212> TYPE: DNA
<213> ORGANISM: Artificial Sequence
<220> FEATURE:
<223> OTHER INFORMATION: Primers and adapters

<400> SEQUENCE: 66
aatgatacgg cgaccaccga gatctacact ggtcacgacg taaaacgacg gccagt   56

<210> SEQ ID NO 67
<211> LENGTH: 56
<212> TYPE: DNA
<213> ORGANISM: Artificial Sequence
<220> FEATURE:
<223> OTHER INFORMATION: Primers and adapters

<400> SEQUENCE: 67
aatgatacgg cgaccaccga gatctacaca ttggccgacg taaaacgacg gccagt   56

<210> SEQ ID NO 68
<211> LENGTH: 56
<212> TYPE: DNA
<213> ORGANISM: Artificial Sequence
<220> FEATURE:
<223> OTHER INFORMATION: Primers and adapters

<400> SEQUENCE: 68
aatgatacgg cgaccaccga gatctacacg atctgcgacg taaaacgacg gccagt   56

<210> SEQ ID NO 69
<211> LENGTH: 56
<212> TYPE: DNA
<213> ORGANISM: Artificial Sequence
<220> FEATURE:
<223> OTHER INFORMATION: Primers and adapters

<400> SEQUENCE: 69
```
aatgatacgg cgaccaccga gatctacact caagtcgacg taaaacgacg gccagt        56

<210> SEQ ID NO 70
<211> LENGTH: 56
<212> TYPE: DNA
<213> ORGANISM: Artificial Sequence
<220> FEATURE:
<223> OTHER INFORMATION: Primers and adapters

<400> SEQUENCE: 70
aatgatacgg cgaccaccga gatctacacc tgatccgacg taaaacgacg gccagt        56

<210> SEQ ID NO 71
<211> LENGTH: 49
<212> TYPE: DNA
<213> ORGANISM: Artificial Sequence
<220> FEATURE:
<223> OTHER INFORMATION: Primers and adapters

<400> SEQUENCE: 71
caagcagaag acggcatacg agatcacaca ggaaacagct atgaccatg               49

<210> SEQ ID NO 72
<211> LENGTH: 21
<212> TYPE: DNA
<213> ORGANISM: Artificial Sequence
<220> FEATURE:
<223> OTHER INFORMATION: Primers and adapters

<400> SEQUENCE: 72
cgacgtaaaa cgacggccag t                                              21

<210> SEQ ID NO 73
<211> LENGTH: 21
<212> TYPE: DNA
<213> ORGANISM: Artificial Sequence
<220> FEATURE:
<223> OTHER INFORMATION: Primers and adapters

<400> SEQUENCE: 73
cctaattccc cccatcctta c                                              21

<210> SEQ ID NO 74
<211> LENGTH: 21
<212> TYPE: DNA
<213> ORGANISM: Artificial Sequence
<220> FEATURE:
<223> OTHER INFORMATION: Primers and adapters

<400> SEQUENCE: 74
actggccgtc gttttacgtc g                                              21

<210> SEQ ID NO 75
<211> LENGTH: 77
<212> TYPE: DNA
<213> ORGANISM: Artificial Sequence
<220> FEATURE:
<223> OTHER INFORMATION: Primers and adapters

<400> SEQUENCE: 75
ggttacaggc tcatgatgta acctctgtgt cttggtgtaa ctttaaaaca tatttttgcc    60
attaccaagc tggtatc                                                   77

<210> SEQ ID NO 76
<211> LENGTH: 77

-continued

<212> TYPE: DNA
<213> ORGANISM: Artificial Sequence
<220> FEATURE:
<223> OTHER INFORMATION: Primers and adapters

<400> SEQUENCE: 76
ggttacaggc tcatgatgta acctctgtgt cttggtgsaa ctttaaaaca tatttttgcc    60
attaccaagc tggtatc                                                  77

<210> SEQ ID NO 77
<211> LENGTH: 55
<212> TYPE: DNA
<213> ORGANISM: Artificial Sequence
<220> FEATURE:
<223> OTHER INFORMATION: Primers and adapters
<221> NAME/KEY: misc_feature
<222> LOCATION: (1)...(55)
<223> OTHER INFORMATION: n = A,T,C or G

<400> SEQUENCE: 77
acactctttc cctacacgac gctcnnnnnn nnnnnnggtg agtctgtgca ggcat         55

<210> SEQ ID NO 78
<211> LENGTH: 45
<212> TYPE: DNA
<213> ORGANISM: Artificial Sequence
<220> FEATURE:
<223> OTHER INFORMATION: Primers and adapters

<400> SEQUENCE: 78
ctcgagcact gtcctgactg agacgatacc agcttggtaa tggca                   45

<210> SEQ ID NO 79
<211> LENGTH: 59
<212> TYPE: DNA
<213> ORGANISM: Artificial Sequence
<220> FEATURE:
<223> OTHER INFORMATION: Primers and adapters

<400> SEQUENCE: 79
aatgatacgg cgaccaccga gatctacacc gtgatacact ctttccctac acgacgctc    59

<210> SEQ ID NO 80
<211> LENGTH: 48
<212> TYPE: DNA
<213> ORGANISM: Artificial Sequence
<220> FEATURE:
<223> OTHER INFORMATION: Primers and adapters

<400> SEQUENCE: 80
caagcagaag acggcatacg agatctcgag cactgtcctg actgagac               48

<210> SEQ ID NO 81
<211> LENGTH: 24
<212> TYPE: DNA
<213> ORGANISM: Artificial Sequence
<220> FEATURE:
<223> OTHER INFORMATION: Primers and adapters

<400> SEQUENCE: 81
acactctttc cctacacgac gctc                                          24